(12) United States Patent
Lonky

(10) Patent No.: US 9,895,140 B1
(45) Date of Patent: Feb. 20, 2018

(54) FRICTIONAL TRANS-EPITHELIAL TISSUE DISRUPTION COLLECTION APPARATUS AND METHOD OF INDUCING AN IMMUNE RESPONSE

(71) Applicant: HISTOLOGICS, LLC, Anaheim, CA (US)

(72) Inventor: Neal M Lonky, Yorba Linda, CA (US)

(73) Assignee: HISTOLOGICS, LLC, Yorba Linda, CA (US)

(*) Notice: Subject to any disclaimer, the term of this patent is extended or adjusted under 35 U.S.C. 154(b) by 0 days.

(21) Appl. No.: 15/068,301

(22) Filed: Mar. 11, 2016

Related U.S. Application Data

(63) Continuation of application No. 14/262,179, filed on Apr. 25, 2014, now Pat. No. 9,282,951, which is a continuation of application No. 13/072,773, filed on Mar. 28, 2011, now Pat. No. 8,795,197, which is a continuation-in-part of application No. 12/669,638, filed as application No. PCT/US2008/070341 on Jul. 17, 2008, now Pat. No. 8,652,067.

(60) Provisional application No. 60/950,280, filed on Jul. 17, 2007.

(51) Int. Cl.
*A61B 10/02* (2006.01)

(52) U.S. Cl.
CPC .. *A61B 10/0291* (2013.01); *A61B 2010/0216* (2013.01)

(58) Field of Classification Search
CPC ........ A61B 2010/0216; A61B 10/0291; A61B 18/0061; A61B 18/0053; A61B 17/32–2017/320012
USPC .................................................. 600/569, 572
See application file for complete search history.

(56) References Cited

U.S. PATENT DOCUMENTS

| | | |
|---|---|---|
| 2,675,572 A | 4/1954 | Nomiya |
| 2,717,437 A | 9/1955 | De Mestral |
| 2,839,049 A | 6/1958 | Maclean |
| 2,955,591 A | 10/1960 | Maclean |
| 3,554,185 A | 1/1971 | Kohl |
| 3,559,226 A | 2/1971 | Burns |
| 3,628,522 A | 12/1971 | Kato |

(Continued)

FOREIGN PATENT DOCUMENTS

| | | |
|---|---|---|
| AT | 392411 | 5/1988 |
| CH | 653880 | 1/1986 |

(Continued)

OTHER PUBLICATIONS

Blute, Renal brush biopsy: Survey of indications, techniques and results, J Urol., Aug. 1981, vol. 126(2), pp. 146-149.

(Continued)

*Primary Examiner* — Michael C Stout
(74) *Attorney, Agent, or Firm* — Sci-Law Strategies, PC

(57) ABSTRACT

In an embodiment of the invention, a frictional tissue sampling device with a head designed to be rotated without rotating off the designated site can be used to obtain tissue biopsy samples. A frictional tissue sampling device with a head designed to be rotated without rotating off the designated site can be used to obtain an epithelial tissue biopsy sample from lesions. The device can be otherwise used to sample specific locations. In various embodiments, the head of the device is narrow and pointed with a hybrid pear shaped diamond facet. Abrasive material can be adhered to the facet.

21 Claims, 27 Drawing Sheets

(56) References Cited

U.S. PATENT DOCUMENTS

| | | | |
|---|---|---|---|
| 3,774,590 A | 11/1973 | McDonald | |
| 3,777,743 A | 12/1973 | Binard | |
| RE27,915 E | 2/1974 | Kohl | |
| 3,796,211 A | 3/1974 | Kohl | |
| 3,877,464 A | 4/1975 | Vermes | |
| 3,945,372 A | 3/1976 | Milan | |
| 4,016,865 A * | 4/1977 | Fredricks | A61B 10/0291 600/570 |
| 4,061,146 A | 12/1977 | Baehr | |
| 4,168,698 A | 9/1979 | Ostergard | |
| 4,227,537 A | 10/1980 | Suciu | |
| 4,384,587 A | 5/1983 | Milgrom | |
| 4,396,022 A | 8/1983 | Marx | |
| 4,430,076 A | 2/1984 | Harris | |
| 4,465,072 A | 8/1984 | Taheri | |
| 4,641,662 A * | 2/1987 | Jaicks | A61B 10/0291 600/570 |
| D289,926 S | 5/1987 | Lonky | |
| 4,700,713 A * | 10/1987 | Kist | A61B 10/0291 15/207.2 |
| 4,754,764 A * | 7/1988 | Bayne | A61B 10/0291 15/106 |
| 4,757,826 A | 7/1988 | Abdulhay | |
| 4,759,376 A * | 7/1988 | Stormby | A46B 9/02 15/206 |
| 4,762,133 A * | 8/1988 | Bayne | A61B 10/0291 15/164 |
| 4,763,669 A | 8/1988 | Jaeger | |
| 4,777,947 A | 10/1988 | Zwick | |
| 4,781,202 A | 11/1988 | Janese | |
| 4,872,243 A | 10/1989 | Fischer | |
| 4,873,992 A * | 10/1989 | Bayne | A61B 10/0291 15/206 |
| 4,892,831 A * | 1/1990 | Wong | C12M 33/02 422/504 |
| 4,932,857 A | 6/1990 | Nishino | |
| 4,946,389 A | 8/1990 | Weissenberger | |
| 4,951,684 A * | 8/1990 | McMillan | A61B 10/0291 600/571 |
| 4,961,430 A | 10/1990 | Sheahon | |
| 4,965,725 A | 10/1990 | Rutenberg | |
| 5,022,408 A * | 6/1991 | Mohajer | A61B 10/02 600/569 |
| 5,067,195 A | 11/1991 | Sussman | |
| 5,069,224 A | 12/1991 | Zinnanti, Jr. | |
| 5,084,005 A * | 1/1992 | Kachigian | A61B 10/02 600/569 |
| 5,092,345 A | 3/1992 | Sakita | |
| 5,133,361 A | 7/1992 | Cox | |
| 5,184,626 A * | 2/1993 | Hicken | A61B 10/0291 600/569 |
| 5,191,899 A | 3/1993 | Strickland | |
| 5,217,023 A * | 6/1993 | Langdon | A61B 10/04 600/569 |
| 5,253,652 A | 10/1993 | Fast | |
| 5,257,182 A | 10/1993 | Luck | |
| 5,259,391 A * | 11/1993 | Altshuler | A61B 10/0291 600/572 |
| 5,279,307 A * | 1/1994 | Mohajer | A61B 10/0291 600/570 |
| 5,287,272 A | 2/1994 | Rutenberg | |
| 5,315,740 A | 5/1994 | Provost | |
| 5,329,938 A | 7/1994 | Lonky | |
| 5,370,128 A | 12/1994 | Wainwright | |
| 5,370,653 A * | 12/1994 | Cragg | A61B 17/22 600/569 |
| 5,421,346 A | 6/1995 | Sanyal | |
| 5,445,164 A | 8/1995 | Worthen | |
| 5,456,265 A | 10/1995 | Yim | |
| 5,462,063 A * | 10/1995 | Kist | A61B 10/02 600/569 |
| 5,464,409 A | 11/1995 | Mohajer | |
| 5,470,308 A | 11/1995 | Edwards | |
| 5,476,104 A | 12/1995 | Sheahon | |
| 5,477,863 A * | 12/1995 | Grant | A61B 10/0096 600/572 |
| 5,535,756 A * | 7/1996 | Parasher | A61B 10/02 600/569 |
| 5,544,650 A | 8/1996 | Boon | |
| 5,549,563 A | 8/1996 | Kroner | |
| 5,623,941 A * | 4/1997 | Hedberg | A46B 3/02 600/569 |
| 5,643,307 A | 7/1997 | Turkel | |
| 5,649,943 A | 7/1997 | Amoils | |
| 5,702,413 A * | 12/1997 | Lafontaine | A61B 17/22 606/159 |
| 5,713,369 A | 2/1998 | Tao | |
| 5,722,423 A | 3/1998 | Lind | |
| 5,738,109 A | 4/1998 | Parasher | |
| 5,761,760 A | 6/1998 | Dumler | |
| 5,785,785 A | 7/1998 | Chesley | |
| 5,792,160 A | 8/1998 | Weiss | |
| 5,795,309 A * | 8/1998 | Leet | A61B 10/0291 600/569 |
| 5,800,362 A | 9/1998 | Kobren | |
| 5,807,282 A | 9/1998 | Fowler | |
| 5,857,982 A | 1/1999 | Milliman | |
| 5,865,765 A | 2/1999 | Mohajer | |
| 5,868,668 A | 2/1999 | Weiss | |
| 5,899,850 A | 5/1999 | Ouchi | |
| 5,913,857 A | 6/1999 | Ritchart | |
| 5,937,870 A | 8/1999 | Gueret | |
| 5,951,550 A | 9/1999 | Shirley | |
| 6,036,658 A * | 3/2000 | Leet | A61B 10/0291 600/569 |
| 6,053,877 A | 4/2000 | Banik | |
| 6,132,421 A | 10/2000 | Clapham | |
| 6,193,674 B1 * | 2/2001 | Zwart | A61B 10/0291 600/569 |
| 6,258,044 B1 | 7/2001 | Lonky | |
| 6,297,044 B1 * | 10/2001 | Eisen | A61B 10/02 382/133 |
| 6,336,905 B1 | 1/2002 | Colaianni | |
| 6,346,086 B1 | 2/2002 | Maksem | |
| 6,346,087 B1 * | 2/2002 | Peltier | A61B 10/0096 600/569 |
| 6,376,905 B2 | 4/2002 | Hisano | |
| 6,379,315 B1 | 4/2002 | Claren | |
| 6,387,058 B1 | 5/2002 | Wallach | |
| 6,394,966 B1 * | 5/2002 | Gill | A61B 10/0045 600/569 |
| 6,491,692 B1 * | 12/2002 | Meislin | A61B 17/16 15/22.2 |
| 6,494,845 B2 | 12/2002 | Rutenberg | |
| 6,595,947 B1 * | 7/2003 | Mikszta | A61B 17/205 604/27 |
| 6,676,609 B1 | 1/2004 | Rutenberg | |
| 6,730,085 B2 | 5/2004 | George | |
| 6,740,049 B2 | 5/2004 | Wallach | |
| 6,821,264 B1 * | 11/2004 | Khurana | A61K 48/0075 514/44 R |
| 6,860,738 B2 | 3/2005 | Bachmann | |
| 7,004,913 B1 * | 2/2006 | Rutenberg | A61B 10/04 600/562 |
| 7,137,956 B2 | 11/2006 | Nishtalas | |
| 7,156,814 B1 | 1/2007 | Williamson, IV | |
| 7,157,233 B2 | 1/2007 | Fischer | |
| 7,413,551 B2 | 8/2008 | Decker | |
| 7,698,772 B1 * | 4/2010 | Hauser, Jr. | A46B 3/18 15/167.1 |
| 7,749,173 B2 | 7/2010 | Larkin | |
| 7,871,574 B2 * | 1/2011 | Peltier | A61B 10/00 422/536 |
| 8,152,739 B1 * | 4/2012 | McCully | A61B 10/0291 600/569 |
| 8,439,847 B2 | 5/2013 | Larkin | |
| 8,652,067 B2 | 2/2014 | Lonky | |
| 8,795,197 B2 | 8/2014 | Lonky | |
| 9,044,213 B1 | 6/2015 | Lonky | |
| 9,282,951 B2 | 3/2016 | Lonky | |
| 9,393,394 B2 | 7/2016 | Lonky | |

(56) References Cited

U.S. PATENT DOCUMENTS

| | | | |
|---|---|---|---|
| 9,687,642 B2 | 6/2017 | Lonky | |
| 2001/0022063 A1 | 9/2001 | Korteweg | |
| 2002/0068881 A1* | 6/2002 | Kobren | A61B 10/0291 600/569 |
| 2002/0161313 A1* | 10/2002 | Sak | A61B 10/0045 600/569 |
| 2003/0034583 A1* | 2/2003 | Provost | A44B 18/0003 264/146 |
| 2003/0055373 A1* | 3/2003 | Sramek | A61B 10/025 604/19 |
| 2003/0109804 A1 | 6/2003 | Auerbach | |
| 2004/0029658 A1 | 2/2004 | Howe | |
| 2004/0120989 A1 | 4/2004 | Vadas | |
| 2004/0116827 A1* | 6/2004 | Tiberio | A61B 10/0045 600/569 |
| 2004/0181170 A1 | 9/2004 | Wallach | |
| 2004/0220478 A1 | 11/2004 | Wallace | |
| 2004/0236247 A1* | 11/2004 | Rizvi | A61B 10/0045 600/569 |
| 2004/0260199 A1 | 12/2004 | Hardia | |
| 2004/0260201 A1 | 12/2004 | Mueller | |
| 2004/0267191 A1 | 12/2004 | Gifford | |
| 2005/0059905 A1 | 3/2005 | Boock | |
| 2005/0215920 A1 | 9/2005 | Isa | |
| 2005/0251093 A1 | 11/2005 | Abou-Kansoul | |
| 2006/0130266 A1* | 6/2006 | Brown | A61B 17/20 15/329 |
| 2006/0200043 A1 | 9/2006 | Jannetty | |
| 2007/0093727 A1 | 4/2007 | Feuer | |
| 2007/0100335 A1 | 5/2007 | Fischer | |
| 2007/0107155 A1 | 5/2007 | Kacher | |
| 2007/0161042 A1 | 7/2007 | Zuk | |
| 2007/0198028 A1* | 8/2007 | Miloslayski | A61B 17/221 606/127 |
| 2007/0282223 A1 | 12/2007 | Larkin | |
| 2008/0077046 A1* | 3/2008 | Burg | A61B 10/0291 600/569 |
| 2008/0188769 A1* | 8/2008 | Lu | A61B 10/02 600/569 |
| 2008/0262384 A1* | 10/2008 | Wiederkehr | G01N 33/57411 600/569 |
| 2008/0294067 A1* | 11/2008 | Zwart | A61B 10/00 600/569 |
| 2009/0012424 A1 | 1/2009 | Huschmand | |
| 2009/0112239 A1 | 4/2009 | To | |
| 2009/0149860 A1 | 6/2009 | Scribner | |
| 2009/0326414 A1 | 12/2009 | Peltier | |
| 2010/0210968 A1 | 8/2010 | Lonky | |
| 2010/0249649 A1* | 9/2010 | Larkin | A61B 10/02 600/569 |
| 2011/0172557 A1 | 7/2011 | Lonky | |
| 2011/0268610 A1 | 11/2011 | Recknor | |
| 2013/0267870 A1 | 10/2013 | Lonky | |
| 2014/0128773 A1 | 5/2014 | Lonky | |
| 2014/0358158 A1 | 12/2014 | Einarsson | |
| 2016/0100862 A1 | 4/2016 | Parys | |
| 2017/0021151 A1 | 1/2017 | Lonky | |

FOREIGN PATENT DOCUMENTS

| | | | |
|---|---|---|---|
| EP | 2166965 | 7/2008 | |
| WO | WO2005084555 | 9/2005 | |
| WO | WO 2006058989 A1 * | 6/2006 | A61B 10/00 |
| WO | WO2007101994 | 9/2007 | |
| WO | WO2009012392 | 1/2009 | |
| WO | WO2012125757 | 9/2012 | |
| WO | WO2015134568 | 9/2015 | |

OTHER PUBLICATIONS

Boon et al., "Confocal Sectioning of Thick, Otherwise Undiagnosable Cell Groupings in Cervical Smears" Acta Cytol., vol. 37, pp. 40-48 (1991).

Boon et al., "Exploiting the "Toothpick Effect" of the Cytobrush by Plastic Embedding of Cervical Samples" Acta Cytol., vol. 35, pp. 57-63 (1991).

Boon, "A model for quantitative follow-up studies of cervical lesions," Diagn Cytopathol., 1992, vol. 8(1), pp. 8-17.

Butler, B., "Kuper brush in the diagnosis of endometrial lesions," The Lancet, Dec. 1971, vol. 298(7739), pp. 1390-1392.

DeGirolami, "Histo-brush technic for endometerial tissue study," Obstet Gynecol., Dec. 1961, vol. 28(6), pp. 861-866.

Dowlatshahi et al., "Evaluation of brush cytology as an independent technique for detection of esophageal carcinoma" J Thoracic and Cardiovascular Surgery, vol. 89, No. 6, pp. 848-851, Jun. 1985.

Fennessy, "Transbronchial biopsy of peripheral lung lesions," Radiology, May 1967, vol. 88(5), pp. 878-882.

Firestone, "Needle lung biopsy, bronchial brushing and mediastinoscopy in Management of Chest Diseases," Calif Med., Sep. 1973, vol. 119(3), pp. 1-5.

Gahres et al., "Histo-brush technic for Endometrial Tissue Study", Obstet Gynecol vol. 28, pp. 861-866 (1966)—Front Page Only.

Goldstein, "Esophageal biopsy utilizing a flexible brush," Gastrointest Endosc., Aug. 1968, vol. 15(1), pp. 53-55.

Granqvist, "Colonoscopic biopsies and cytological exam in chronic ulcerative colitis," J Gastroenterology, Apr. 1980, vol. 15(3), pp. 283-288.

Hardwick, "Brush biopsy in the diagnosis of neoplasia in Bartlett's esophagus," Disease Esophagus, Oct. 1997, vol. 10(4), pp. 233-237.

Iaccarino, "Percutaneous intralesional brushing of cystic lesions of bone: a technical improvement of diagnostic cytology," Skeletal Radiol, 1990, vol. 19(3), pp. 187-190.

International Search Report of PCT/US2008/70341 published as WO2009012392 dated Oct. 22, 2008.

Johnsson, "Cytological brush techniques in malignant disease of the endometrium," Acta Obstet Gynecol Scand, Jan. 1968, vol. 47, issue 1, pp. 38-51.

Johnsson, "Cytological diagnosis of endometrial disorders with a brush technique," Acta Obstet Gynecol Scand., 1971, vol. 50(2), pp. 141-148.

Kovnat, "Bronchial brushing through the flexible fiberoptic bronchoscope in the diagnosis of peripheral pulmonary lesions," Chest, Feb. 1975, vol. 67(2), pp. 179-184.

Liu, "Transcervical chorionic villus biopsy with a brush," Prenat Diagn., Sep.-Oct. 1985, vol. 5(5), pp. 349-355.

Maksem, "Endometrial brush cytology of advanced postmenopausal endometrium . . . ," Diagn Cytopathol., Nov. 1998, vol. 19(5), pp. 338-343.

Matsuda, "Bronchial brushing and bronchial biopsy: comparison of diagnostic accuracy and cell typing reliability in lung cancer," Thorax, Jun. 1986, vol. 41(6), pp. 475-479.

Meulman, "Predictions of various grades of cervical neoplasia on plastic-embedded cytobrush samples," Anal Quant Cytol Histol., Feb. 1992, vol. 14(1), pp. 60-72.

Mills, "Transcatheter brush biopsy of intravenous tumor thrombi," Radiology, Jun. 1978, vol. 127(3), pp. 667-670.

Morteza, "Brush and forceps biopsy of billary ducts via percutaneous transhepatic catheterization," Radiology, Jun. 1980, vol. 135, pp. 777-778.

Moskowitz, "To brush or not to brush is there really a question?," Chest, Jun. 1971, vol. 59(6), pp. 648-650.

Mullins, "A new technique for transbronchial biopsy in infants and small children," Pediatr Pulmonol, Oct. 1995, vol. 20(4), pp. 253-257.

Payne, "Diagnostic accuracy of cytology and biopsy in primary bronchial carcinoma," Thorax, Jun. 1979, vol. 43(3), pp. 294-299.

Pipkorn, "A brush to harvest cells from the nasal mucosa for microscopic and biochemical analysis," J Immunol Methods, Aug. 9, 1988, vol. 112(1), pp. 37-42.

Portner, "New devices for biliary drainage and biopsy," Radiology, Jun. 1982, vol. 138, pp. 1191-1195.

Raney, "Detection of carcinoma of upper urinary tract with steerable brush biopsy," Urology, Jul. 1979, vol. 14(1), pp. 77-78.

(56) References Cited

OTHER PUBLICATIONS

Ravinsky, "Cytologic features of primary adenoid cystic carcinoma of the uterine cervix. A case report," Acta Cytol., Nov.-Dec. 1996, vol. 40(6), pp. 1304-1308.
Riise et al., "Bronchial brush biopsies for studies of epithelial inflammation in stable asthma and nonobstructive chronic bronchitis" Eur Respir J vol. 9, pp. 1665-1671 (1996).
Riise, "A bronchoscopic brush biopsy study of large airway mucosal pathology in smokers . . . ," Eur Respir J., Apr. 1992, vol. 5(4), pp. 382-386.
Roth et al., "Cytologic Detection of Esophageal Squamous Cell . . ." Cancer, vol. 80, No. 11, Dec. 1, 1997.
Sanderson, "Use of a new controllable-tip brush with the flexible fiber bronchoscope," Chest, Jun. 1974, vol. 65(6), pp. 620-621.
Sheline, "Fluoroscopically guided retrograde brush biopsy in the diagnosis of transitional cell carcinoma of the upper urinary tract . . . ," Am J Roentgenology, Sep. 1989, vol. 153(2), pp. 313-316.
Willson, "Bronchial brush biopsy with a controllable brush," Am J Roentgenology, Jul. 1970, vol. 109(3), pp. 471-477.
Zavala, "Use of Bronchofiberscope for bronchial brush biopsy: diagnostic results and comparison with other brushing techniques," Chest, Jun. 1973, vol. 63(6), pp. 889-892.
Zeppa, "A model for quantitative follow-up studies of cervical lesions," Diagn Cytopathol, 1992, vol. 8(1), pp. 8-17.
International Search Report, PCT/US2008/070341, dated Oct. 22, 2008.
Extended European Search Report, PCT/US2008/070341, dated May 11, 2012, 7 pages.
Australian Patent Exam Report 20130806, dated Aug. 6, 2013, 5 pages.
European Office Action, 08796246.0-1654, dated Jun. 5, 2015, 5 pages.
Article 94(3) European Communication, Application No. 08796246.0 PCT/US2008/070341, dated Jul. 4, 2016, 4 pages.
International Search Report, PCT/US2017/014190, dated Apr. 10, 2016, 13 pages.

\* cited by examiner

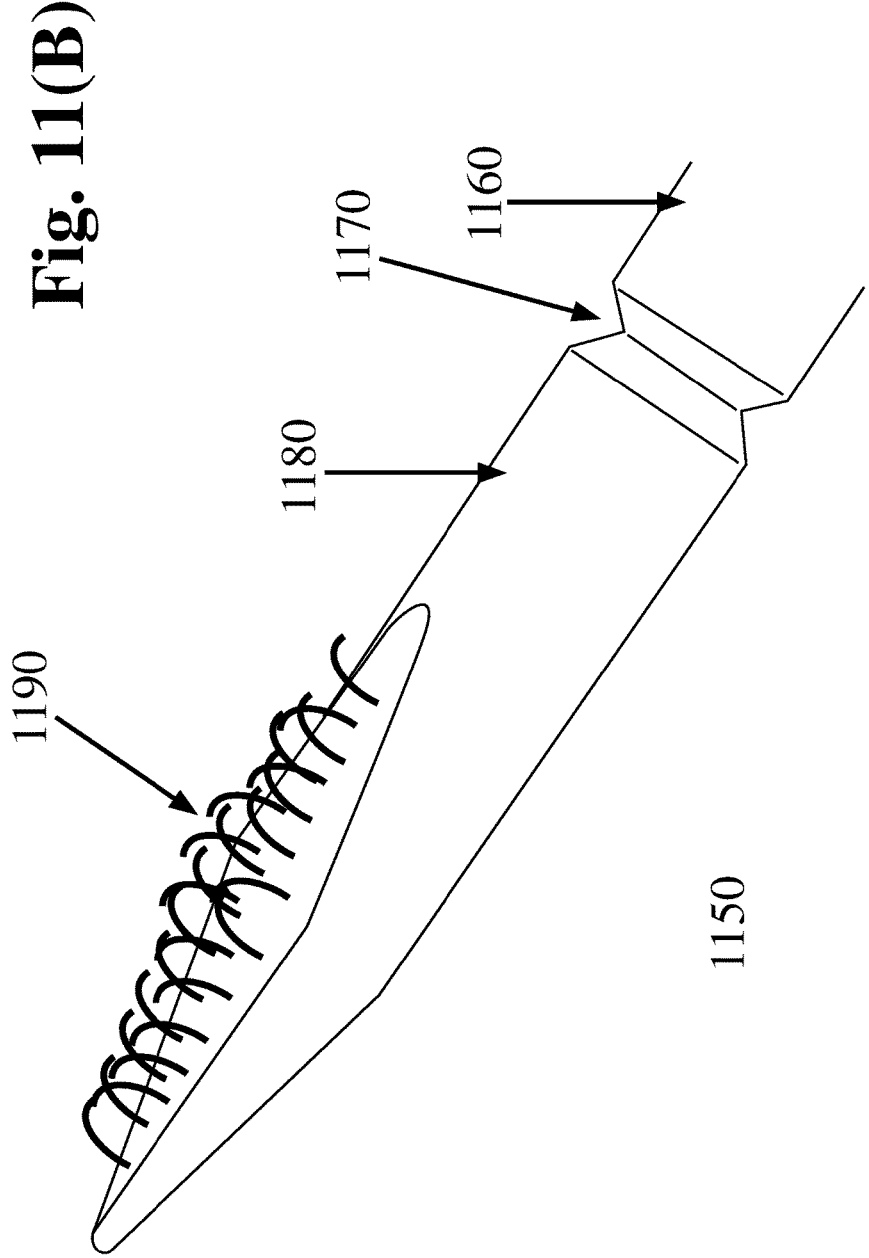

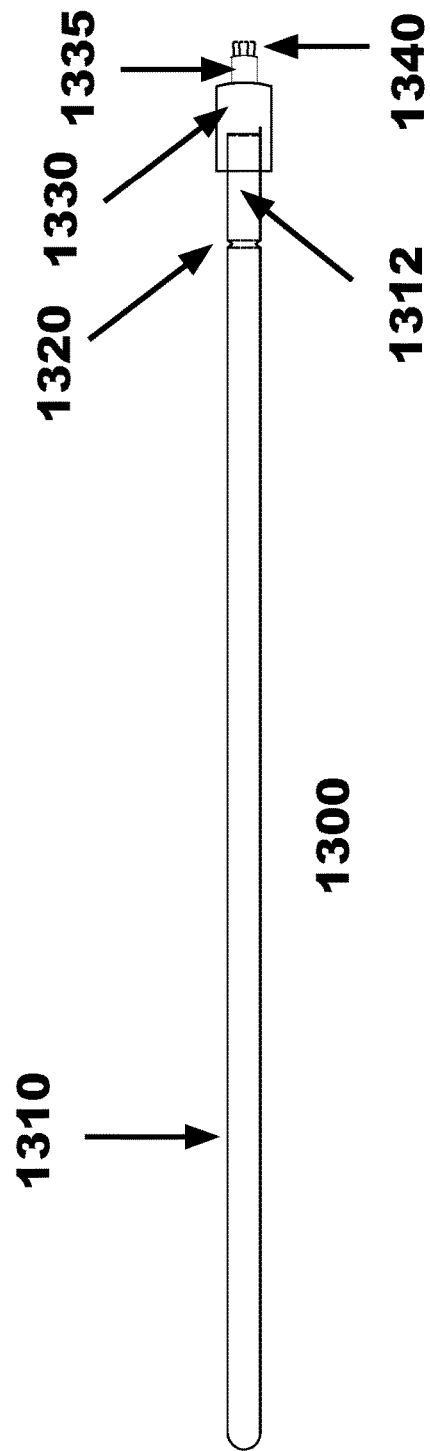

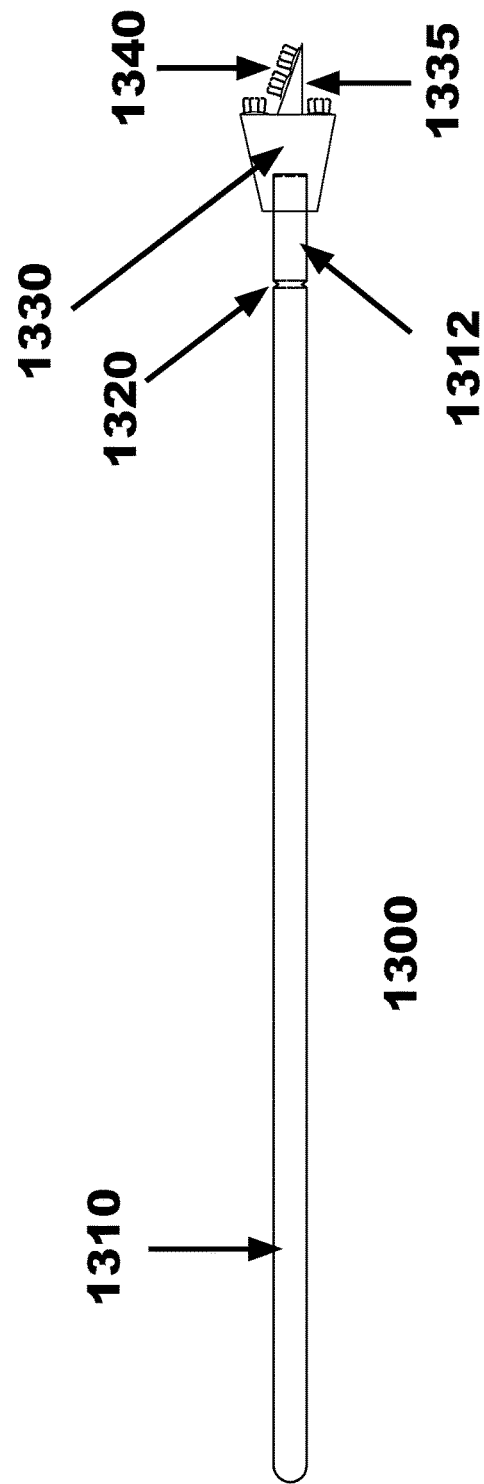

FRICTIONAL TRANS-EPITHELIAL TISSUE DISRUPTION COLLECTION APPARATUS AND METHOD OF INDUCING AN IMMUNE RESPONSE

PRIORITY CLAIM

This application is a continuation of and claims priority to (1) U.S. Utility application Ser. No. 14/262,179 entitled "FRICTIONAL TRANS-EPITHELIAL TISSUE DISRUPTION COLLECTION APPARATUS AND METHOD OF INDUCING AN IMMUNE RESPONSE" filed Apr. 25, 2014 which is a continuation of and claims priority to (2) U.S. Utility application Ser. No. 13/072,773 filed Mar. 28, 2011 entitled "FRICTIONAL TRANS-EPITHELIAL TISSUE DISRUPTION AND COLLECTION APPARATUS AND METHOD OF INDUCING AND/OR AUGMENTING AN IMMUNE RESPONSE", which issued as U.S. Pat. No. 8,795,197 on Aug. 5, 2014, which is a continuation-in part (CIP) of and claims priority to (3) U.S. Utility application Ser. No. 12/669,638 filed Jan. 19, 2010 entitled "FRICTIONAL TRANS-EPITHELIAL TISSUE DISRUPTION AND COLLECTION APPARATUS AND METHOD OF INDUCING AND/OR AUGMENTING AN IMMUNE RESPONSE", which issued as U.S. Pat. No. 8,652,067 on Feb. 18, 2014 and which was the National Phase of (4) Patent Cooperation Treaty Application US08/70341 filed Jul. 17, 2008 which claimed priority to (5) U.S. Provisional Application No. 60/950,280 entitled "FRICTIONAL TRANS-EPITHELIAL TISSUE DISRUPTION AND COLLECTION APPARATUS AND METHOD OF INDUCING AND/OR AUGMENTING AN IMMUNE RESPONSE", filed Jul. 17, 2007. The U.S. Utility application Ser. No. 13/072,775 filed Mar. 28, 2011 also claimed priority to (6) U.S. Provisional Application No. 61/318,128, entitled "FRICTIONAL TISSUE SAMPLING AND COLLECTION METHOD AND DEVICE" filed Mar. 26, 2010. Each of these applications (1)-(6) are herein expressly incorporated by reference in their entirety.

FIELD OF THE INVENTION

The invention relates to epithelial tissue sampling and collection devices for performing biopsies from lesions and anatomical landmarks at risk of neoplastic transformation, including but not limited to the squamo-columnar junction of the female cervix, methods of inducing an immune response against a pathogen and methods of trans-epithelial drug delivery.

BACKGROUND OF THE INVENTION

A lesion is caused by any process that alters or damages tissue. A lesion can be defined as any pathological or traumatic discontinuity of tissue with partial loss of tissue function. The concept of a lesion includes wounds, sores, ulcers, tumors, cataracts and any other tissue damage. Lesions can range from the skin sores associated with eczema to the changes in lung tissue that occur in tuberculosis. Generally, a lesion can be characterized by the epithelium covering the connective tissue becoming fragile, leading to ulceration and bleeding.

Previous devices include brushes with rigid bristles that puncture and shear epithelial surfaces (U.S. Pat. Nos. 5,535,756; 6,258,044; 6,376,905; 6,494,845 and 6,132,421), single metal or plastic curettes that extend in a parallel direction to the applicator handle and are much larger than the innovation (U.S. Pat. Nos. 4,641,662 and 6,730,085), scalpels or similar bladed sharp cutting tools (U.S. Pat. Nos. 5,857,982; 5,800,362; 3,774,590; 5,092,345; 4,061,146; 5,868,668; 6,053,877; 5,470,308; 7,137,956, 4,168,698 and 4,757,826; and U.S. Publication Nos. 2005/0059905 and 2007/0093727), or very large electrified metal loops used to produce excisional biopsies (U.S. Pat. Nos. 5,913,857 and 5,951,550). One device performs simultaneous brush cytology and scrape biopsy on structures with an organic duct (U.S. Pat. No. 5,535,756). U.S. Pat. No. 5,643,307 "Colposcopic Biopsy Punch with Removable Multiple Sample Basket" has also been proposed to obtain biopsy samples when examining the cervix.

Human papillomaviruses (HPV) are responsible for many cutaneous and mucosal lesions. Some viral genotypes are considered to be the causal agents of cervical cancer. Natural genital HPV infection seems to be poorly immunogenic because of its nonproductive and non-inflammatory characteristics and also because of mechanisms developed by the virus to counteract the immune response.

Cervicovaginitis refers to inflammation of the squamous epithelium of the vagina and cervix caused by an inflammatory reaction to an infection. This damage leads to desquamation and ulceration, which can cause a reduction in the epithelial thickness due to loss of superficial and part of the intermediate layers of cells. In the deeper layers, the cells are swollen with infiltration of neutrophils in the intercellular space. The surface of the epithelium is covered by cellular debris and inflammatory mucopurulent secretions. The underlying connective tissue is congested with dilatation of the superficial vessels and with enlarged and dilated stromal papillae. Rare and uncommon cervical infections, due to tuberculosis, schistosomiasis and amoebiasis, cause extensive ulceration and necrosis of the cervix with symptoms and signs mimicking invasive cancer. Herpes simplex virus (HSV) can be present on the mucosal lining of the mouth or genitals. A large coalesced ulcer due to HSV can also mimic the appearance of invasive cancer. Chronic inflammation causing recurrent ulceration and healing of the cervix, can result in a distortion of the cervix. Infections with the pathogenic fungi *Cryptococcus neoformans*, *Histoplasma capsulatum*, and *Coccidioides immitis* can be disseminated and some, e.g., *C. neoformans*, can result in pneumonia or meningitis. Longstanding viral, bacterial, fungal or protozoal infection and inflammation may lead to white or pink appearance as a result of fibrosis.

SUMMARY OF THE INVENTION first aspect relates to a fabric for functionally abrading epithelial surfaces including a backing material and a plurality of fenestrated loops attached to the backing material, the loops having sufficient flexibility and rigidity to frictionally abrade the epithelial surfaces, wherein the loops are about 3 mm to about 25 mm in length, wherein the loops have a short hook end, and wherein the distance from the top of the loop to the bottom of the hook is less than 50% of the length of the loop.

A second aspect relates to an apparatus for obtaining a histological sample including a handle, a platform at a distal end of the handle, and a fabric for functionally abrading epithelial surfaces including a backing material and a plurality of fenestrated loops attached to the backing material.

A third aspect relates to a method of inducing an immune response against a pathogen that normally evades the immune system including disrupting epithelial cells containing the pathogen with a frictional trans-epithelial tissue disruption apparatus, and thereby introducing the pathogen, DNA fragments, proteins or antigenic material into the bloodstream of a patient to elicit an immune response.

A fourth aspect relates to a method of trans-epithelial drug delivery including disrupting tissue with a trans-epithelial tissue disruption apparatus and applying a drug to intra-epithelial and sub-epithelial spaces created by the disrupting tissue.

There is significant incentive for being able to obtain a biopsy sample of cells from a lesion in a manner which involves minimal pain and in the least intrusive manner. In an embodiment of the present invention, an apparatus for obtaining a biopsy sample includes a handle, a flat, concave or convex surface at a distal end of the handle, and a fabric for functionally abrading tissue surfaces applied to the surface. In an embodiment of the present invention, an apparatus for obtaining a histological sample includes a handle, a flat, concave or convex surface at a distal end of the handle, and a fabric for functionally abrading epithelial surfaces. In an alternative embodiment of the present invention, an apparatus for obtaining a histological sample includes a handle, a flat, concave or convex surface at a distal end of the handle, and a fabric for functionally abrading epithelial surfaces including a backing material and a plurality of fenestrated loops attached to the backing material. A concave surface with an adherent abrasive fabric allows the handle to be rotated and remain on the desired location to collect a biopsy from convex tissue surfaces. A convex surface with an adhered abrasive fabric allows the hand to be rotated and remain on the desired location to collect a biopsy from concave tissue surfaces. A flat surface with an adherent abrasive fabric allows the hand to be rotated and pressed completely without allowing gaps between the abrasion material and a flat surface tissue to be sampled when collecting a biopsy.

BRIEF DESCRIPTION OF THE DRAWINGS

This invention is described with respect to specific embodiments thereof. Additional features can be appreciated from the Figures in which:

FIG. 2(A) shows a side view, FIG. 2(B) shows an oblique view, FIG. 2(C) shows a top view;

FIG. 3(A) shows a flat epithelial surface. FIG. 3(B) shows an epithelial surface of a canal or body cavity;

FIG. 6(A) shows a representation of tissue with a squamous epithelial lined surface. FIG. 6(B) shows an application of the frictional biopsy device to the body surface. FIG. 6(C) Simultaneous pressure, agitational, and rotational force splays and separates the hooks/loops. Frictional abrasive forces create heat which buckles the epithelial surface. FIG. 6(D) Sufficient abrasion creates shearing and fracture of the epithelial surface at varying depths which could include fracture through the basement membrane into the subcutaneous layer. FIG. 6(E) The hooks insinuate into the fracture plane, and with additional abrasive forces continue to shear the tissue fragments, while simultaneously retaining the tissue for capture and collection. FIG. 6(F) At the completion of the biopsy process, the collection of hooks arranged in rows create channels which collect and sequester the tissue and cell cluster fragments within the channels created in the device. When the device is removed from the epithelial surface, additional sample is captured and held due to the flexibility and recoil of the hooks;

FIG. 11(B) is an expanded side view of an endo-cervical FTSC head with a single diamond shaped facet in accordance with an embodiment of the invention;

FIG. 13(A) is a side view of an FTSC device with a cylinder extending from the distal surface of a disc and the disc connected to the handle and the collection material attached on the distal surface of the cylinder in accordance with an embodiment of the invention;

FIG. 13(H) is a side view of an FTSC device with a cylindrical facet extending from the distal surface of a cone shaped disc and the disc connected to a handle and the collection material attached on the distal surface of the cylinder in accordance with an embodiment of the invention;

DETAILED DESCRIPTION OF THE INVENTION

Definitions

Figure 1:
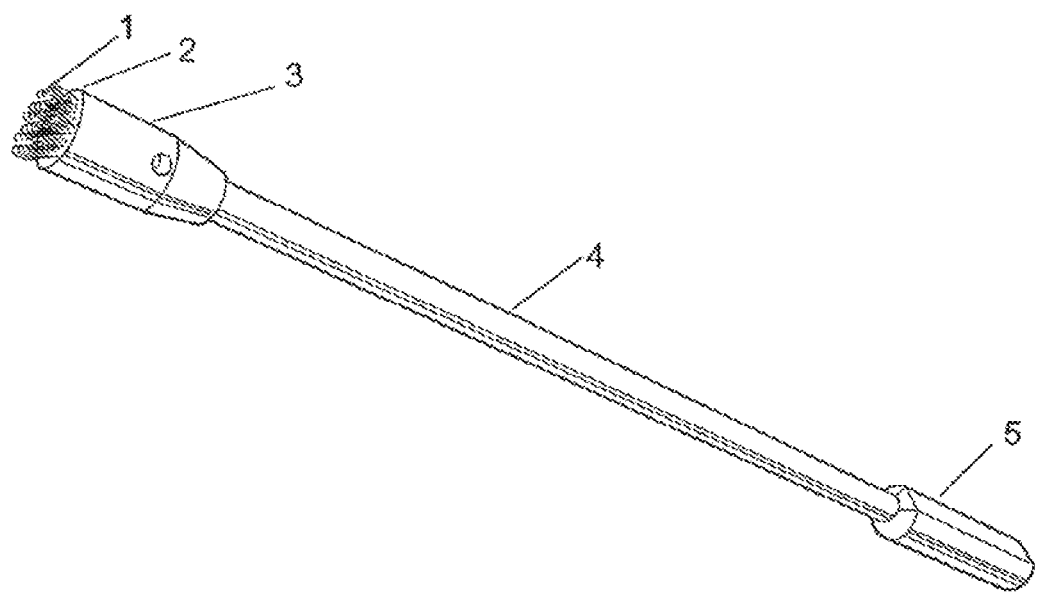
FIG. 1 is an apparatus for frictional trans-epithelial tissue disruption of an epithelial flat surface.

The transitional term "comprising" is synonymous with "including," "containing," or "characterized by," is inclusive or open-ended and does not exclude additional, unrecited elements or method steps.

The transitional phrase "consisting of" excludes any element, step, or ingredient not specified in the claim, but does not exclude additional components or steps that are unrelated to the invention such as impurities ordinarily associated with a composition.

The transitional phrase "consisting essentially of" limits the scope of a claim to the specified materials or steps and those that do not materially affect the basic and novel characteristic(s) of the claimed invention.

As used herein, the term "abrasive material" refers to "toothbrush" bristle brush design, twisted strands of metal wire, twisted strands of plastic fibers, steel wool, corrugated plastic, Velcro® and Kylon®. As used here the term "fenestrated loop" refers to a hooked, "candy-cane" shape formed by severing a loop, wherein a short, hooked end is less than approximately 50% of the length of the loop. In some embodiments, a fenestrated loop is formed by severing a loop once, leaving a short arm adjacent to the fenestrated loop.

A 'facet' is a surface that is cut into the head of a biopsy device, where the surface's contour differs from the contour of the head of the biopsy device. The term 'facet' is used in analogy to a facet of a gem, where the gem facet has a surface contour that differs from the other surface contours of the other facets of the gem. A facet that is cut at an angle of 30 degrees relative to the major axis of the head of the biopsy device is equivalent to a 'point' cut in a gem that can produce one side of an octahedron. A facet that is cut at an angle of 3-9 degrees relative to the major axis of the head of the biopsy device can be thought of as equivalent to one of the 30 odd cuts in a gem's crown to produce a 'brilliant'. In contrast to the facet of a gem which is typically flat, the facet cut in the head of a biopsy device can have a flat, concave or convex surface contour. That is a flat facet of a biopsy device has neither a positive nor a negative radius of curvature. A convex facet of a biopsy device has a positive radius of curvature relative to the flat facet. A concave facet of a biopsy device has a negative radius of curvature relative to the flat facet. The curvature of a cylinder or rod will be referred to as positive in contrast to the negative curvature of a concave facet cut into the cylinder or rod. The curvature of a convex facet cut into the cylinder or rod will be referred to as positive.

The maximum overall diameter of a FTSC device with one facet is the sum of the maximum diameter of the head and the length of the abrasive material attached to the facet. The overall diameter of a FTSC device at a point on the one facet is the sum of the diameter of the head at that point and the length of the abrasive material attached to the facet.

In the following description, various aspects of the present invention will be described. However, it will be apparent to those skilled in the art that the present invention may be practiced with only some or all aspects of the present invention. For purposes of explanation, specific numbers, materials, and configurations are set forth in order to provide a thorough understanding of the present invention. However, it will be apparent to one skilled in the art that the present invention may be practiced without the specific details. In other instances, well-known features are omitted or simplified in order not to obscure the present invention.

Parts of the description will be presented in data processing terms, such as data, selection, retrieval, generation, and so forth, consistent with the manner commonly employed by those skilled in the art to convey the substance of their work to others skilled in the art. As is well understood by those skilled in the art, these quantities (data, selection, retrieval, generation) take the form of electrical, magnetic, or optical signals capable of being stored, transferred, combined, and otherwise manipulated through electrical, optical, and/or biological components of a processor and its subsystems.

Various operations will be described as multiple discrete steps in turn, in a manner that is most helpful in understanding the present invention; however, the order of description should not be construed as to imply that these operations are necessarily order dependent.

Various embodiments will be illustrated in terms of exemplary classes and/or objects in an object-oriented programming paradigm. It will be apparent to one skilled in the art that the present invention can be practiced using any number of different classes/objects, not merely those included here for illustrative purposes.

Systems and methods in accordance with embodiments of the present invention can provide for improved presentation and interaction with digital content and representations of digital content. Representation as used herein includes, but is not limited to, any visual and/or audible presentation of digital content. By way of a non-limiting example, digital images, web pages, digital documents, digital audio, and other suitable content can have corresponding representations of their underlying content. Moreover, interfaces such as graphical user interfaces can have corresponding representations of their underlying content.

The invention is illustrated by way of example and not by way of limitation in the figures of the accompanying drawings in which like references indicate similar elements. It should be noted that references to 'an' or 'one' embodiment in this disclosure are not necessarily to the same embodiment, and such references mean at least one.

A biopsy can resolve the causative agent in many if not all of the lesions that are formed from viral, bacterial, fungal or protozoal infections. In the case of HSV, the sample must include cells, not just fluid from the blister, since the virus is in the skin cells of the blister or ulcer. The sample from a lesion or blister collected during an acute outbreak can be used to identify the agent based on the growth of the virus or substances related to the virus.

Plex ID™ is a high-throughput system based on polymerase chain reaction (PCR) and mass spectrometry analysis to enable identification of pathogens within six to eight hours. Plex ID™ can detect and characterize a broad range of microorganisms in a given sample, including viruses, bacteria and fungi. Although Plex ID™ is not currently intended for use in diagnostic procedures, it is available for use in unregulated areas such as epidemiologic surveillance, biological research, environmental testing, and forensic research. Plex ID™ has been shown to detect viral isolates from adenovirus, alphavirus, enterovirus, flavivirus, HSV and human parvovirus B19 with a limit of detection ranging from 15 to 125 copies.

Focal Biopsy

Some embodiments relate to a trans-epithelial, frictional tissue sampling and collection device to perform biopsies of lesions suspected of harboring disease. In some embodiments, a lesional biopsy site is no larger than about 10 mm in diameter (i.e., focal biopsy). In some embodiments the lesions are accessible to an examiner during routine examination. In other embodiments, the surface is accessible following entry into a body cavity through a natural orifice or surgical channel via a trochar and inspection using an endoscope with a biopsy port. The device head remains on the lesion or area of intended biopsy/therapy due to the rigid nature of the applicator. Referring to FIG. 7, a focal biopsy apparatus is configured with loops that are about 3 mm to about 25 mm in length, preferably about 3 mm in length, wherein the loops have a short hook end, wherein the distance from the top of the loop to the bottom of the hook is less than 50% of the length of the loop.

Regional Biopsy

In some embodiments, the intent is to biopsy and screen large geographic areas of tissue at risk for disease (e.g., neoplastic transformation such as, but not limited to, the squamo-columnar junction of the female cervix in the presence or absence of visualized lesions). The device provides samples of clumps or clusters of excavated epithelial tissue fragments for analysis, in contrast to other methods disclosed in prior art that provide surface and exfoliated cells by sweeping the cells from such target tissue sites, commonly with blunt spatula or soft bristle brush devices. The intent is to remove tissue based evidence with frictional biopsy of the larger area, which may range from 10-40 millimeters in diameter.

Simultaneous Biopsy of Epithelial Surfaces and Canal-Like Structures

In some embodiments, the device contains a central core of longer fenestrated loops (e.g., about 4-7 mm long), surrounded by a wider rim of shorter fenestrated loops (e.g., about 3 mm in length). The longer loops are geometrically suited to insinuate within a central canal structure, such as the endocervical canal of the cervix. There is simultaneously uniform contact of the fenestrated loop fibers circumferentially around the endocervical canal on the flat exocervical surface. With rotation and agitation in a back-and-forth motion, tissue is harvested within the fenestrated loop channels as described above.

Referring to FIG. 8, a central disc of fibers insinuates into a canal surrounded by a perimeter of shorter fibers. In one embodiment, 9 mm long central fibers are surrounded by 3 mm fibers. An apparatus with these parameters may be inserted on/into cervix and rotated with spinning revolutions. Following frictional trans-epithelial tissue disruption, the head containing biopsy sample may be detached and inserted into a liquid vial of fixative.

Frictional Tissue Sampling and Collection Biopsy Devices

The frictional tissue sampling and collection biopsy devices disclosed herein utilize a fabric that includes minute plastic (e.g., nylon) fiber loops that are fenestrated at a minimal distance from the apex of the loop. The loops flex but do not fracture under minimal to moderate force or separate under pressure.

The semi-rigid loops may be pressed in a rotational manner (e.g., in sweeping or circular motion) away from or toward the operator, perpendicular, or at an angle into epithelial tissue surfaces. The semi-rigid loops remain flexible enough to cause separation of the fenestrated ends, creating frictional forces sufficient to cause local heating and buckling of the epithelial surface away from the underlying stroma. The loops are fenestrated such that with applied pressure they are flexible enough to open and provide access to a "collection well" for histological fragments. The tips of the fiber hooks are oriented away from the tissue. On pressing and rotation across the tissue surface, the fibers scrape, buckle and shear the epithelium from the underlying stroma. The fragments are excoriated from the tissue surface through the concomitant application of frictional forces applied to the tissue surfaces by the fenestrated loops. The frictional forces overcome the adhesive and binding forces of the tissue below to release fragments of various shapes and size, all eligible for collection in a histology lab, and subsequent processing and analysis.

The semi-rigid loops (e.g., made of nylon) hold the tissue fragments after excoriation because the loops are elastic enough to sufficiently re-close and capture the remove tissue. In addition, the spaces between the fibers also retain excoriated tissue. The frictional forces exceed the binding forces afforded by adhesion molecules which anchor epithelia to the basement membrane, as well as disrupting Van der Waals forces.

Once the epithelium is frictionally sheared from the underlying stroma, the tissue clumps and epithelial fragments are swept and excavated by the distal most curved apex of the loop and entrapped within the geometrically suited spaces between the closed, fenestrated loops. Thus, the method is frictional abrasion, excavation via rotation and other directional motion, and tissue collection within interloop channels.

The fabric can be cut into uniform shapes such as a circular disc or straight edge shape(s) and with uniform height, allowing the device to provide 360 degree coverage of tissue surfaces over suspected lesions, without a gap within the circumference of the device. This is in distinction to bristle brushes which are spiral or bent in shape, which present surface gaps that do not allow uniforms contact with the target tissue, and gaps that cause migration of the device from the lesion site toward the direction of rotation when such devices are pressed onto lesions and rotated or moved for tissue harvesting.

Following biopsy, the fabric, fibers, and/or device head (all with the tissue entrapped between the fibers) are removed and placed in a vial of liquid fixative for later laboratory work. A laboratory may remove the tissue from the device and process it for analysis. Therefore, one may intentionally design the device in an embodiment in which the user could easily decouple the device head from the device shaft. For example, some embodiments may have the shaft inserted into the head via a clip or screw thread mechanism, a key-in-lock design with a pressure release button, or a luer-lock type of attachment. Once the biopsy is obtained, the head and handle/shaft parts can be de-coupled, wherein the handle can be discarded, or sterilized and re-used, and the head immersed in a vial of fixative.

Some methods for removal of tissue from the fiber assembly include rinsing under pressure, immersion and agitation manually or mechanically, or by sonication. Alternatively, the fibers can be sheared from the fabric on telfa or other filter paper, and the fibers plucked off the paper leaving the entire biopsy specimen. Alternatively, after tissue is collected into the device channels, tissue may deposited via rotation or agitation in a vial of liquid fixative, rinsed off the device under pressurized spraying, or removed from the nylon fibers by cutting away the nylon fibers from the fabric (e.g., onto filter paper), thus leaving the tissue on the paper, which can be immersed in fixative.

In preferred embodiments, the fabric fibers are manufactured in a similar manner to Velcro® or other hook and pile type fastener, where strands are longer than conventional hook and pile, about 3 mm in length, fenestrated closer to the apex of the loop instead of close to the base of one arm of the loop, and thus appear V-wishbone shaped. They have a short hook end with the curvature starting at 2 mm from the base. Because the loop strands are longer, they flex and bend to a greater angle and twist with greater elasticity when rotated or agitated when compared with standard Velcro®. Because the fenestration is closer to the base in standard Velcro®, the loops fenestrations are unlikely to separate, leaving the curved smooth surface of the loop in contact with the tissue, not providing sufficient frictional forces during rotation to shear and separate the epithelium form the underlying basement membrane and stroma.

Preferred embodiments utilize minute plastic fenestrated loops that are pressed perpendicular or at an angle into epithelial tissue surfaces which, upon rotational or agitational pressure forces, cause tissue epithelial fragments to be frictionally separated from the underlying tissue basement membrane and stroma. The channels between the fenestrated loops entrap and collect the tissue fragments. The process is similar to curettage with a blunt curved tool, which also scrapes, shears and strips epithelium from the underlying stroma of target tissues. On the other hand, the process is in contrast to sharp curettage where the purposefully sharp edge of the curette first incises, pierces, then shaves and scoops epithelium and underlying stroma from the tissue surface. The process described herein is less perceptible to patients than conventional biopsies and causes a smaller amount of blood loss and trauma.

In one aspect, the present invention relates to a frictional trans-epithelial tissue apparatus. In some embodiments, the apparatus comprises 3 mm or smaller loops adherent to and projecting perpendicular from a platform, with a density of 5-50 loops per square inch, evenly spaced or arranged in rows. The loops may be intact or fenestrated at the center or at their lateral aspect to allow for added flexibility and constructed from plastic, metal, or another stiff material. The rounded end of the loop is opposite the platform.

Loops of sufficient flexibility to withstand frictional forces and not fracture, and of sufficient tensile strength to generate sufficient frictional shear force during a sweeping or circular motion of the device to remove epithelium from tissue. The space between loops may serve to capture and harbor the sampled tissue.

In some embodiments designed for focal lesional biopsy, a flat, flexible platform, which anchors the loops may be of any size, but is most practically approximately 5-10 mm in diameter and circular in shape. The shape may be another geometrical design if it affords an advantage in covering the target tissue area for sampling. The platform may be hinged in such a way that it can be folded or compressed, inserted through a small endoscopic channel, and then reinstated to its original state as a platform with a sampling surface. It may be comprised of plastic, cloth, or another composite material. The loops are threaded through and project away from the platform towards the tissue surface. Some embodiments may comprise a hub fiber or "pin" that penetrates and anchors the center of the disc on the target biopsy area, serving as a central post to rotate the disc around for stability.

In other embodiments intended to screen a larger, regional tissue site at risk for neoplastic transformation or other disease process, the optimal shape is circular, the diameter could range from about 10-50 mm, and the loops project at varied distances from the platform to towards the tissue surface. For the purpose of histological screening to detect cervical neoplasia, the central 5 mm diameter disc projects longer (5-25 mm) fenestrated loop fibers, and is surrounded circumferentially by the aforementioned approximately 3-23 mm long loop fibers. The longer fibers insinuate inside canal structures, (e.g., the endocervical canal) simultaneously with contact of the shorter fibers with an outer endothelial surface (e.g., the exocervical surface). Upon pressure and rotation or agitation, the endocervical and exocervical tissues can be simultaneously frictionally sheared and collected. Histological screening may be necessary to correctly reflect the presence or absence of epithelial pathology, because adhesion molecules may prevent representative exfoliation from diseased tissue in some cases, leaving cytological screening methods lacking in accuracy.

Preferably, a frictional trans-epithelial biopsy sample is taken from a lesion or an anatomical region that is predisposed to disease.

Some embodiments comprise a plastic, metal, or mixed composition cylinder or curved convex head, which provides a flat surface for the platform to be attached to. It is equal or greater in diameter to the platform. The cylinder is 5-10 mm in length while the flat or convex base is less than about 3 mm thick.

Some embodiments comprise a rod or cylindrical shaped applicator probe comprised of any suitable material (e.g., wood, plastic, paper or metal), which has the base, platform and loop unit at its most distal end, wherein the applicator probe is approximately 2-5 mm in diameter and 15-30 cm in length. It is constructed larger or smaller depending on the access to the tissue surface. The shaft of the rod or cylindrical shaped applicator probe may be rigid or semi-rigid so as to not bow or arc when pressure is transmitted from the handle to the device head.

A handle into which the applicator probe can be transfixed is optionally mechanical, providing motorized rotational, drill-like movement or agitating vibration.

The device handle will be composed of stiff material, preferably plastic similar to Lucite, clear or opaque in coloration, rigid nylon plastic, or alternatively could be wood or metal. The device head can take may shapes, cylindrical or tapered in design, but the distal most platform face is circular, square, or polygonal, and may be composed of plastic, (e.g., nylon). The diameter may range from 5-50 mm. The fabric is welded to the nylon platform ultrasonically, or may alternatively be attached via adhesive, or via a rim or collar (e.g., which snaps on to the platform into a recess in the head of the device).

In some embodiments, the operator examines tissue surfaces and chooses an area to be sampled based on the presence of a suspicious lesion. In other embodiments, the operator chooses an anatomical landmark known to be "at risk" for neoplastic or disease transformation for the purposes of sampling the entire chosen surface.

The handle or applicator probe is grasped at its proximal end or handle.

The distal portion or head of the device that contains the base, platform and loops that project perpendicular from the base towards the tissue surface with the more rounded ends that are pressed against the tissue surface.

With moderate pressure, the examiner simultaneously presses and rotates the device against the tissue several times in a clockwise or counterclockwise direction, opening or separating the fenestrated loops, thus performing frictional disruption of the tissue surface. Alternatively, a sweeping motion may be used. If a motorized handle is used, it can be activated to assist in the rotation or vibration of the device.

The harvested tissue is collected from the tissue surface, and some tissue already trapped in the loops themselves is inspected and can be teased from the loops, or the loops transected from the fabric and separated, and the remaining tissue placed in a fixative solution.

Figure 3A:
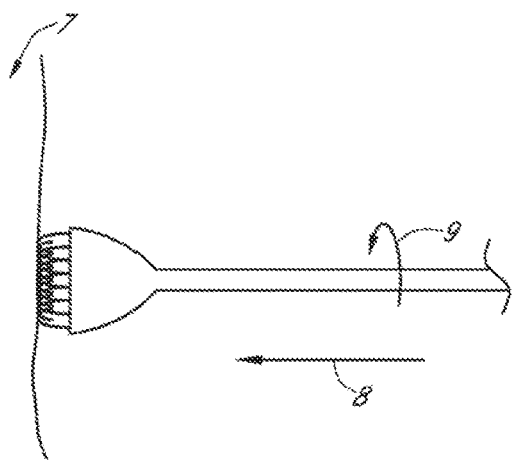
FIGS. 3(A)-(B) shows a schematic diagram of a method of frictional trans-epithelial tissue disruption.

As shown in FIG. 1, fabric with fenestrated loops (1) is connected to platform (2), which is in communication with head (3), located at a distal end of handle (5), optionally including an elongated rod (4). Referring to FIG. 3A, moderate force (8) is applied against a tissue surface (7). The device head is rotated (9) on the surface to frictionally separate or agitate the surface epithelium. The device head is rinsed or placed with tissue in the loops into fixative for subsequent pathological analysis.

Figure 2A:
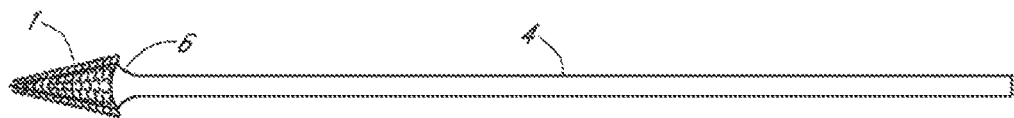
FIGS. 2(A)-(C) shows an apparatus for frictional trans-epithelial tissue disruption of an epithelial lined canal surface with tapered cone tip.
Figure 2B:
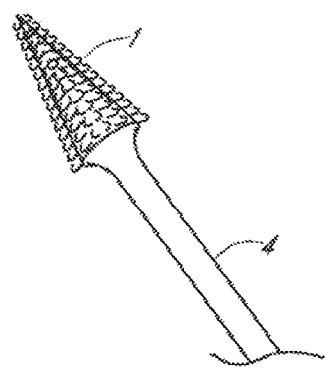
Figure 2C:
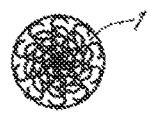
Figure 3B:
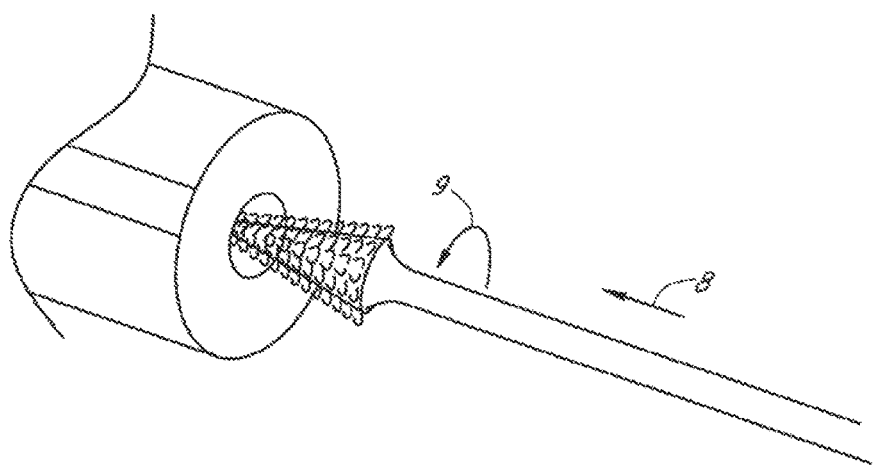

An apparatus with a conical platform is depicted in FIG. 2. In FIG. 2A, fabric with fenestrated loops (1) is connected to conical platform (6). Referring to FIG. 3B, an apparatus with a conical platform may be inserted into a canal or cavity. The device head is rotated (9) while maintaining pressure force in direction (8). The device head with tissue in the loops is rinsed or placed into pathological fixative.

Figure 4:
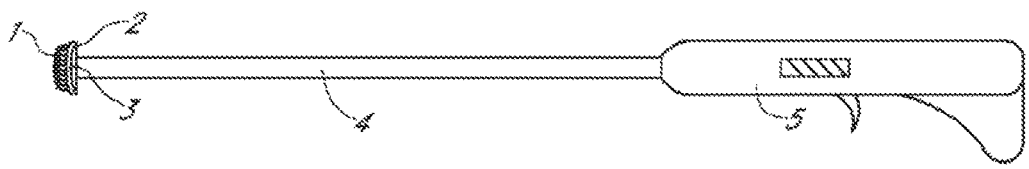
FIG. 4 is a frictional trans-epithelial tissue disrupter with a motorized or vibratory handle used to spin or agitate the fenestrated loops.

An apparatus with a motor configured to rotate the platform is depicted in FIG. 4. Fabric with fenestrated loops (1) is attached to platform (2) on head (3) at the distal end of an elongated rod (4), which is attached to a motorized handle (5).

Figure 5:
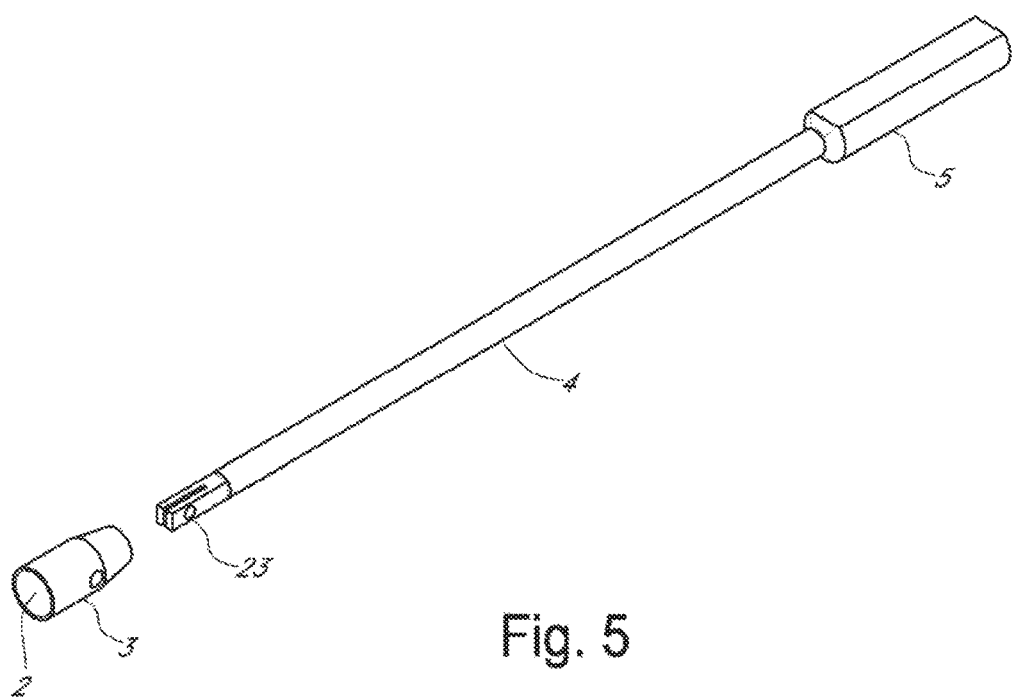
FIG. 5 is a schematic diagram of an apparatus with a detachable platform that anchors fiber loops at a distal end of the handle.
Figure 6A:
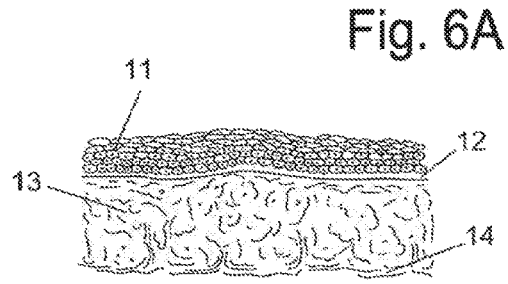
FIGS. 6(A)-(F) shows a schematic diagram of frictional trans-epithelial tissue disruption.
Figure 6B:
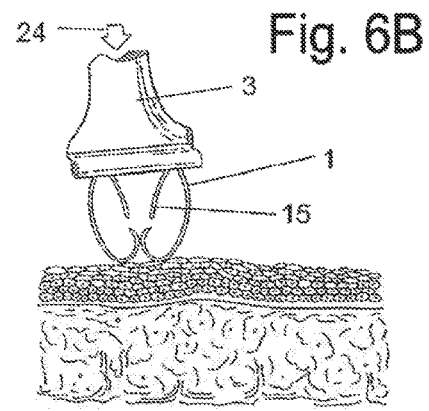
Figure 6C:
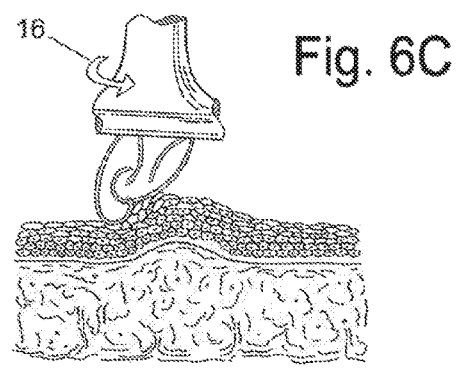
Figure 6D:
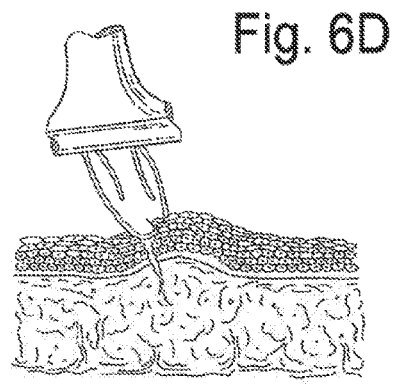
Figure 6E:
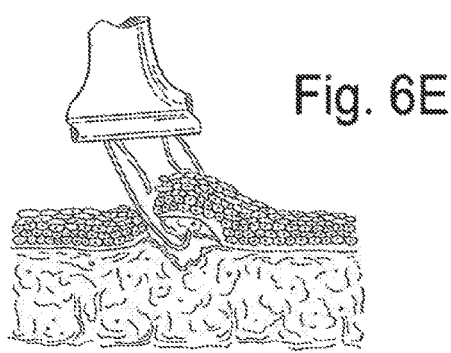
Figure 6F:
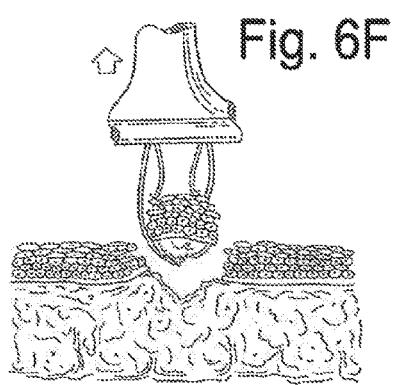

In some embodiments, the head is detachable from the elongated rod/handle. Referring to FIG. 5, a detachable head configuration allows the distal portion with head (3), platform (2), together with attached fabric containing loops, to be detached and placed into a preservative medium for later tissue removal and pathological processing. Some embodiments may have the shaft inserted into the head via a clip or screw thread mechanism, or a luer-lock type of attachment (23). Tissue fragments that remain attached to the detachable head are in addition to any free tissue obtained and collected from the tissue surface or the device as a result of the frictional tissue sampling.

Referring to FIG. 6, epithelial tissue samples are obtained by frictional trans-epithelial tissue disruption. A representation of tissue with a squamous epithelial lined surface is depicted in FIG. 6(A). The squamous epithelial multilayer (11) is shown with superficial flat and basal cuboidal epithelium. Basement membrane (12) separates the squamous epithelial multilayer from the subcutaneous tissue stroma (13) and the underlying sub-stromal tissue (14). FIG. 6B) depicts application of the frictional biopsy device to the tissue surface. The device head (3) is applied (24) to a chosen area where curved portions of the fenestrated loops (1) press against the epithelial surface. A representation of two abutting hooks is shown, creating a collection channel. A shorter arm (15), adjacent to the fenestrated loop (1), may remain following severing of an initial continuous loop to create the fenestrated loop. In FIG. 6C), simultaneous pressure, agitational, and rotational force (16) splays and separates the hooks/loops. Frictional abrasive forces create heat which buckles the epithelial surface. Referring to FIG. (6D), sufficient abrasion creates shearing and fracture of the epithelial surface at varying depths which could include fracture through the basement membrane into the subcutaneous layer. As shown in FIG. 6E), the hooks insinuate into the fracture plane, and with additional abrasive forces continue to shear the tissue fragments, while simultaneously retaining the tissue for capture and collection. At the completion of the biopsy process (see FIG. 6F), the collection of hooks arranged in rows creates channels that collect and sequester the tissue and cell cluster fragments within the channels. When the device is removed from the epithelial surface, additional sample collection is achieved due to the flexibility and recoil of the hooks.

Figure 7A:
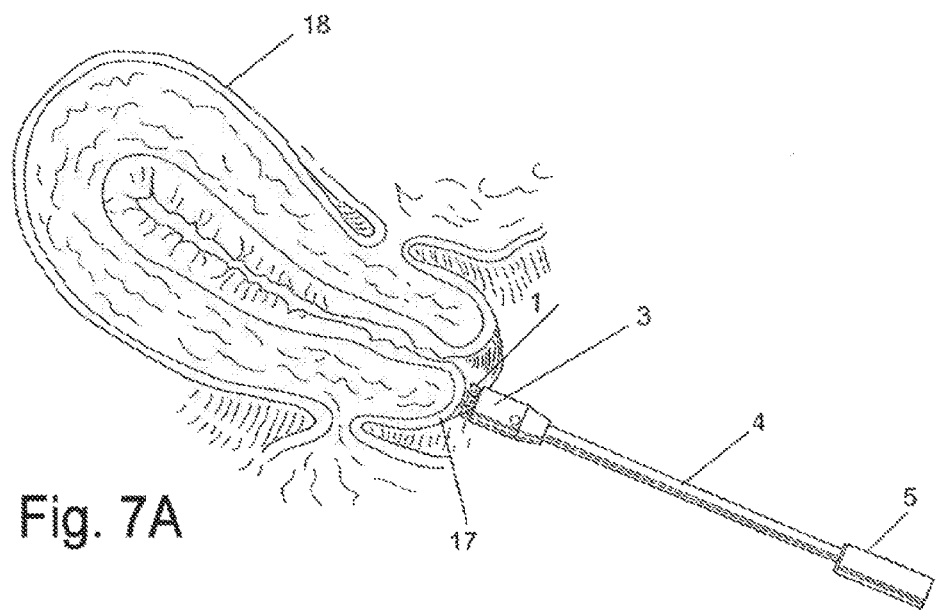
FIG. 7(A) is a side view of a focal biopsy apparatus, depicted at the outer lip of the cervix (exocervix)
Figure 7B:
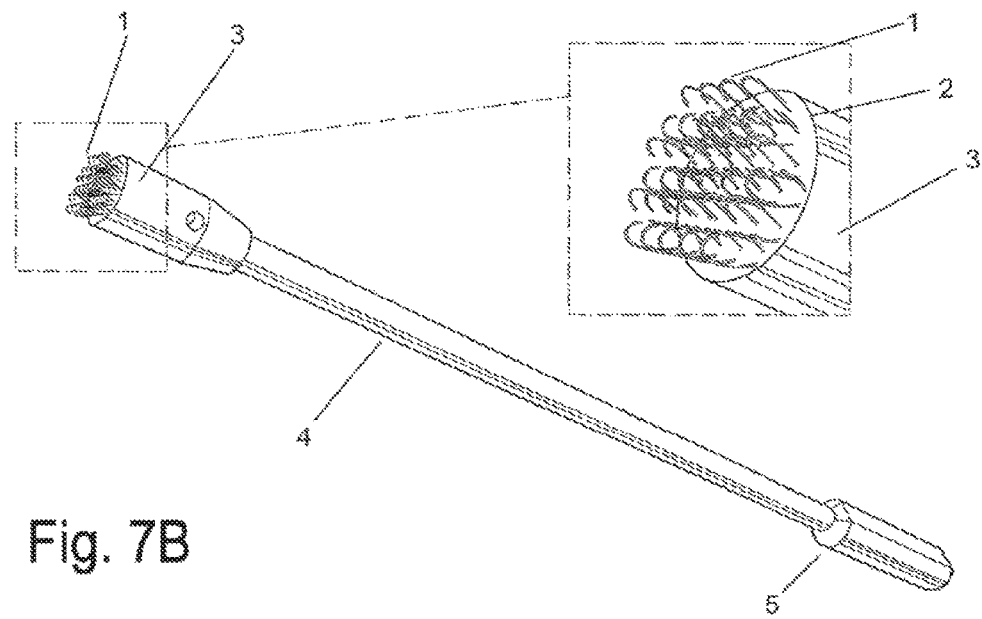
FIG. 7(B) is a schematic diagram of an apparatus for focal biopsies with an enlarged view of the platform and loops.

Referring to FIG. 7A, frictional trans-epithelial tissue disruption with a focal biopsy apparatus is shown at the outer lip of the exocervix (17), alternatively known as the "transformation zone" of the cervix (18). In this configuration, fenestrated loops (1) approximately 3 mm in length are used to disrupt and collect tissue fragments. FIG. 7B depicts an enlarged focal biopsy apparatus, with an enlarged view of fenestrated loops (1) attached to platform (2).

Figure 8A:
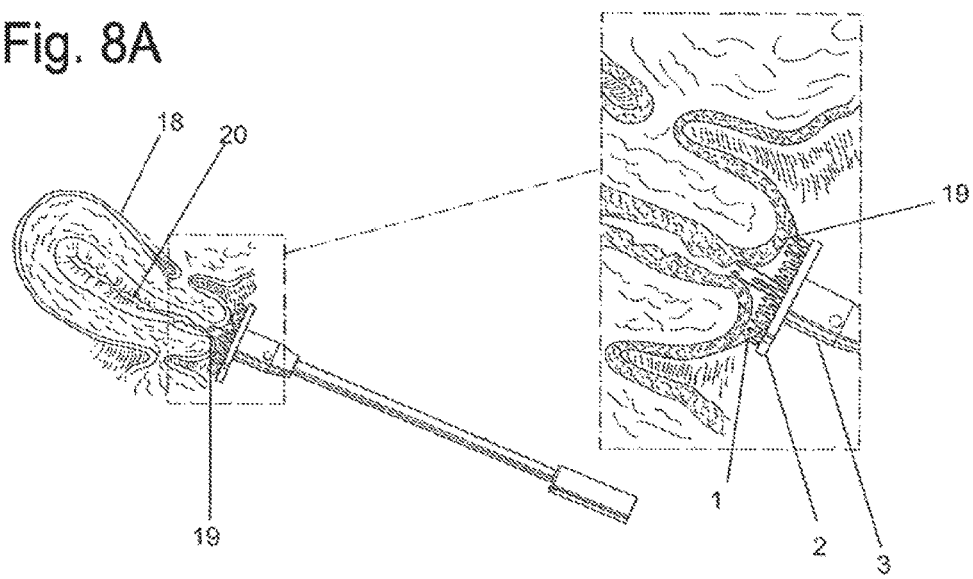
FIG. 8(A) is a side view of an apparatus for simultaneous biopsy of epithelial surfaces and canal-like surfaces. Longer central core fibers to insinuate into a canal and a perimeter of approximately 3 mm fibers contact an outer epithelial surface.
Figure 8B:
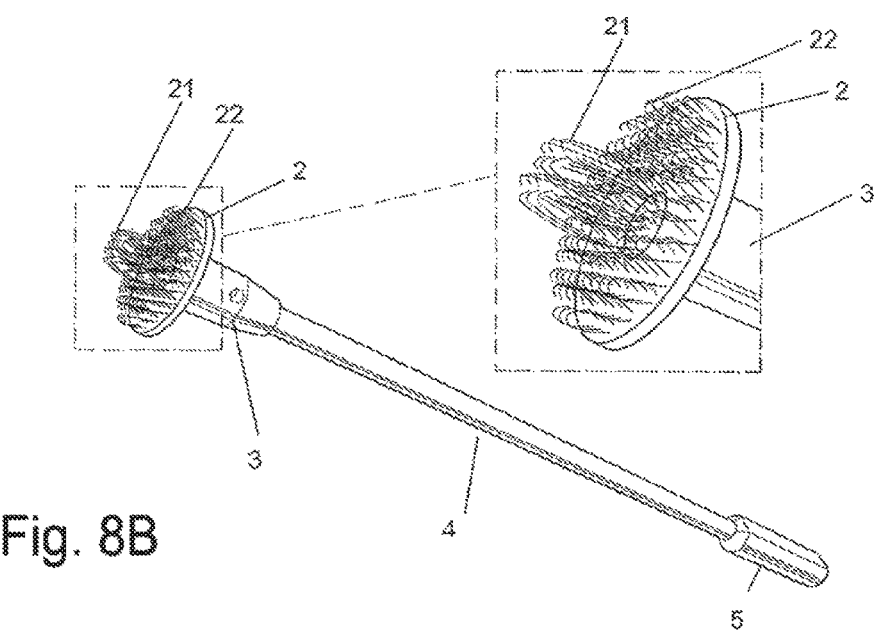
FIG. 8(B) is a schematic diagram of an apparatus for simultaneous biopsy of epithelial surfaces and canal-like surfaces with enlarged view of platform and loops.

Referring to FIG. 8A, simultaneous trans-epithelial biopsy of epithelial surfaces and canal-like surfaces, in particular, biopsy of the endocervical canal (20) and the exocervical area around the endocervical canal (i.e., the transformation zone) is shown (19). Referring to FIG. 8B, a central core of elongated loops of about 5-25 mm in length (21) are surrounded by a wider rim of shorter fenestrated loops of about 3-23 mm in length (22).

The frictional tissue sampling and collection device can be used on any body surface, both external to the body, body cavities, or on internal organs. To access epithelial surfaces of internal body organs, the device head may be deflated, folded or collapsed to pass through a small aperture or port, and re-opened or expanded to fully expose the fabric to the biopsy surface. This device can be used on humans or any other living organism with an epithelial surface. Any tissue surface may be sampled. The ease of use in each case will be related to the strength of the individual tissue adhesion and binding forces in specific locations. The loops themselves can harvest the tissue and also serve as tissue collection reservoirs for later storage once placed in a fixative medium. The platform with the loops may be detached from any applicator for later examination and processing (i.e., decoupled from the instrument used to press against tissue surfaces to obtain the tissue sample).

If the tissue surface is a canal or concave shaped area of the body, instead of a perpendicular platform design, the loops are directly attached to the probe itself which are gradually tapered at the end to facilitate insertion into the canal. The loops project perpendicular from the probe surface at its distal end, and the unit, once placed into the canal that is lined on its surface with epithelium, contacts such epithelium snugly.

The loops can be mounted on the platform or project from the rim surface of the platform, perpendicular or at an angle to the platform along the margin of the platform, or attached to other delivery applicators, including the examiner's gloved finger, or other surgical instruments. The platform can be any shape or size which can fit on a tissue surface. The base assembly can be any shape or size, and may be permanently rigid or collapsible.

If the tissue surface lies within a canal shaped tissue surface, the loops can be attached directly to the applicator probe, which can be inserted into the canal shaped body cavity. The probe with the loops projecting from the surface and contacting the epithelium is rotated causing the frictional disruption sampling from the tissue surface. The shape of the probe can be constructed in any shape that allows a snug fit into the canal. The loops may be arranged in rows or equally spaced, allowing for maximal contact and tissue collection.

Some embodiments of the invention comprise a motorized mechanical assistance via a mechanical handle into which the most proximal end of the applicator probe is inserted. Such mechanical assistance may enhance the rotational or vibratory force that the device transmits to the tissue after contact is established. This can increase the frictional forces and the speed of the tissue disruption/sampling and shorten the procedure time.

Preferred Parameters of Fibers

The frictional sampling loops of the invention are collectively referred to as fenestrated loop fibers. In particularly preferred embodiments, the fibers are made using the hooked side of a modified Velcro® or other hook and pile type fastener, where the strands are about 3 mm in length and are V-wishbone shaped. They have a short hook end with the curvature starting at 2 mm from the base. In various embodiments, the loops may be 2.5-25 mm in length, 3-5 mm in length, 3-10 mm in length, 3-15 mm in length, 3-20 mm in length or 3-25 mm in length.

In comparison, standard Velcro® is about 2 mm long and is more hooked. Thus, the loops of the present invention are longer than those of standard Velcro®, they are made of a similar nylon material compared with standard Velcro®, are more flexible when rubbed on a tissue surface due to their length, and they have shorter loops that hook nearer to the end of the strands. In particular, the distance from the top of the loop to the bottom of the hook is preferably less than 50% of the length of the loop, more preferably less than 40%, still more preferably less than 30%, and even more preferably less than 20% the length of the loop. This distance is also preferably at least 1% the length of the loop, more preferably at least 5% the length of the loop, and still more preferably at least 10% the length of the loop. Thus, the invention includes hooks in all of the ranges between any of the preferred minimum distances and any of the preferred maximum distances. The bottoms of the hooks are preferably arranged so that they are all approximately the same distance from the loop, although this is not strictly necessary. Because the hooks are cut at a relatively distal location, the ends of the hooks are more accessible to the tissue surface allowing for uniform transmission of frictional forces to the tissue surface. As a result, the action of the fibers more effectively buckle and shear the tissue, while the loops sweep over and capture the tissue.

In a preferred embodiment, the loop fibers are arranged so as to efficiently capture tissue. Thus, in one preferred embodiment, the fibers are arranged in an orderly orientation. For example, the fibers can be arranged in rows between which the tissue can be captured. The hooks can be arranged to be at oriented at approximately the same angle and direction in each of the fibers. Thus, the fibers can be organized such they all have a consistent direction and angle of orientation. In addition, the spacing between each of the fibers can be made to be the same or different.

In use, the device can be oriented so that the fibers are perpendicular to tissue, and then pressure is applied. As a result, the epithelial surface is frictionally sheared. Thus, the fibers are preferably mounted on a flat or curved platform, optimally 4-10 mm in diameter so as optimize this process. However, alternatively shaped platforms can also be used in certain embodiments. Because the fibers can be mounted directly on the platform, which may be flat or slightly curved, the orientation remains evenly spaced and the spaces inside the fenestrated loops and between them remain evenly distributed to facilitate tissue capture.

In some embodiments the platform may in the form of a thumbtack, wherein it is attached to the handle. However, the platform and handle may take on a variety of forms. It is envisioned that the handle and the platform may be molded as one piece, and the fibers (e.g., modified Velcro®) may be attached with adhesive or via ultrasonic or thermal welding of the fabric to the platform.

Method of Inducing an Immune Response by Autoinoculation

In some embodiments, the trans-epithelial, frictional tissue sampling and collection devices described herein are utilized to agitate and disrupt epithelial cells containing a pathogen, or cellular proteins altered by a pathogen, to induce an immune response against the pathogen. This results in auto-inoculation of tissues that harbor pathogens and macromolecules such as virally altered DNA and/or oncogenic proteins. The method may also be termed therapeutic frictional abrasion-excoriation. This method is advantageous when a pathogen is normally able to evade an immune response. For example, some viruses remain in surface epithelial layers where they are sequestered from the immune system. Other viruses may be integrated into cellular DNA, thereby evading immune detection.

The methods of inducing an immune response against a pathogen that normally evades the immune system comprise the steps of a) disrupting epithelial cells containing the pathogen, virally altered DNA, or cellular oncoproteins with a micro-curettage device described herein, and b) introducing the pathogen into the bloodstream of a patient to elicit an immune response.

In some embodiments, the trans-epithelial, frictional tissue sampling and collection devices described herein are utilized to disrupt epithelial cells to induce an immune response against human papillomaviruses (HPVs). HPVs are persistent viruses that can remain in their hosts for long periods of time before causing any ill effects. Generally, the host reacts to viral pathogens by generating both humoral and cell-mediated responses. Humoral responses are typically antibody-mediated and involve the secretion of antibodies such as immunoglobulin A (IgA) and immunoglobulin G (IgG) by B lymphocytes. Cell-mediated responses, on the other hand, are carried out by immune effector cells such as dendritic cells (DCs), natural killer (NK) cells, macrophages and T lymphocytes which secrete a number of cytokines including interferons (INF) and tumor necrosis factor (TNF), and up-regulate the expression of Fas ligand (FasL) and TNF-related apoptosis inducing ligand (TRAIL) on their cell surface.

In the case of HPV infection, the immune response is frequently weak or undetectable, and accompanied by little or no inflammation. Even when an immune response is elicited, it may not be able to clear the virus. Disruption of the epithelial surface by frictional tissue disruption induces repair and inflammation and serves to auto-inoculate the patient. Without wishing to be bound by any theory, exposure of the epithelial surface to frictional tissue disruption, uniquely induced by the apparatus and methods disclosed herein through local heating from friction forces exerted, may enhance the induction of repair, inflammation and an immune response following patient autoinoculation. Agitation or scrubbing of a lesion serves to introduce viral particles into the bloodstream of a patient where they can trigger a humoral or antibody related immune response. In addition the method can fracture cells releasing antigens locally within the tissue stroma inducing a cell mediated response associated with the release of cytokines and attraction of helper and killer T cells to the sampled tissue area.

Advantageously, the method of the present invention auto-inoculates a patient with viral particles of the specific viral serotype(s) that the patient is infected with. In contrast, current vaccine strategies are effective on a subset of HPV strains. For example, GARDASIL® by Merck & Co., Inc. is indicated to help prevent cervical cancer, precancerous and low-grade cervical lesions, vulvar and vaginal pre-cancers and genital warts caused by human papillomavirus (HPV) types 6, 11, 16 and 18 and Cervarix™ by GlaxoSmithKline is an HPV 16/18 cervical cancer candidate vaccine. The vaccine is commonly injected in a limb, not the target organ at risk, the cervix, and has been only documented to elicit a humoral antibody immune reaction.

Drug Application

In some embodiments, an adjuvant drug or an immune modulating agent is used in combination with the autoinoculation method, thus augmenting an immune response. For example, Imiquimod (Aldara® topical cream, manufactured and marketed by Graceway Pharmaceutical Company) is approved for the treatment of actinic keratosis, external genital warts and superficial basal cell carcinoma (sBCC), a type of skin cancer. An immune response may be enhanced by using such immune modulating agents in combination with autoinoculation by the methods described herein. The adjuvant drug can be applied to the fenestrated loop fibers directly akin to toothpaste on a toothbrush, or a channel within the applicator can be used to transmit the drug from the top of the handle by means of a squeeze bulb or syringe, through a small lumen in the center of the fabric disc, concomitant with the tissue disruption, delivering drug into the fracture crevices created during the frictional buckling and shearing process created by the device.

Some embodiments comprise a method of drug delivery to a pathological lesion or areas of tissue that concomitantly disrupts tissue planes, creating crevices or pathways for drugs to enter via intra-epithelial and sub-epithelial spaces. This is in contrast to topical therapies, which are slowly absorbed into and through the epithelia. Intra-lesional application is more focused and requires less drug, presenting less risk of side effects.

Any type of drug (e.g., ablative, antibiotic, antiseptic, immune modulating, etc. may be used.

In some embodiments, drug is delivered via an applicator comprising a fabric with fenestrated loops as described herein. Drug is applied in a manner akin to applying toothpaste to a toothbrush, or drug may injected onto the platform or the apparatus via a channel leading through a hollow applicator handle. The drug application apparatus may optionally have an element through which the drug is delivered (e.g., a syringe with a locking mechanism). Drug is applied to a "wound" created by frictionally agitating the tissue. In some embodiments, the fenestrated loops may be impregnated with a drug during manufacture, wherein the drug leeches out into the disrupted tissue when the fiber contacts and macerates/disrupts the tissue.

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

In various embodiments of the present invention, a trans-epithelial Frictional Tissue Sampling and Collection (FTSC) device can be used to perform biopsies of lesions suspected of harboring disease. Clinicians are used to a rotational soft bristle brush to collect endocervical cytology. This soft bristle brush is rotated, with the soft bristles removing superficial cells. When a deeper biopsy is required after an abnormal pap smear or to evaluate the cause of vaginal bleeding, clinicians currently use a sharp edge curette. A sharp edge curette is not designed to and customarily is not rotated to obtain a biopsy. Instead, it is repeatedly inserted, then withdrawn against the canal beginning at a reference point. As the cervix is cylindrical with a circular face, the clinician typically starts at a reference point, usually 12:00 o'clock position, and shift, rotating to all positions around the clock, sequentially back and forth rotated as it is pushed in and pulled back. A clinician may use the sharp curette, most commonly the Kevorkian curette, and scrapes the cervical os surface to accumulate cells. The to and from scraping motion shears epithelium and cells which lie free in the canal and are later collected, as the curette is not also designed to collect the majority of tissue harvested. The procedure with the Kevorkian curette is both painful and can cause trauma to the cervix, as it shaves and detaches the epithelium from the underlying stroma.

Figure 13B:
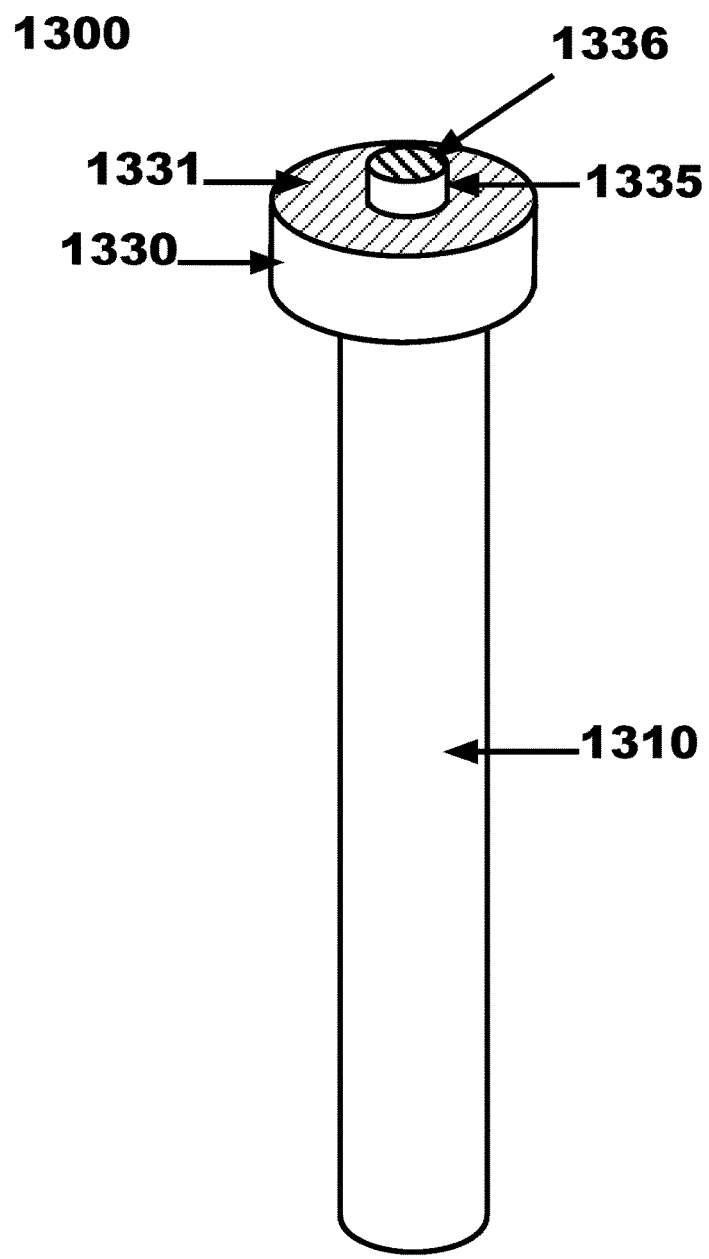
FIG. 13(B) is a side view of an FTSC device with a cylinder extending from the distal surface of a disc and the disc connected to a handle in accordance with an embodiment of the invention.

Currently a clinician can choose a exocervical FTSC or an endocervical FTSC biopsy tool. In an embodiment of the invention, a clinician can choose a hybrid exocervical/endocervical FTSC screening biopsy tool. As shown in FIG. 13(H) in an embodiment of the invention, the clinician fits the cylinder 1335 of the hybrid exocervical/endocervical screening biopsy tool projecting from the larger disk 1330 into the cervical os canal. As shown in FIG. 13(F) in an embodiment of the invention, the surface of one or both the facet 1336 present on the cylinder 1335 and the face 1331 of the disc 1330 contact one or both the squamo-columnar junction and the endocervical columnar epithelium. In an embodiment of the invention, the disc 1330 can have a diameter of approximately 35 mm. In an alternative embodiment of the invention, the disc 1330 can have a diameter of approximately 25 mm. In an embodiment of the invention, the cylinder 1335 can have a diameter of approximately 9 mm. In an embodiment of the invention, the cylinder 1335 can have a diameter of approximately 6 mm. In an embodiment of the invention, the cylinder 1335 can have a diameter of approximately 3 mm.

In an embodiment of the invention, a lesional biopsy site sampled with the FTSC device can be no larger than approximately 3 mm in diameter. In an alternative embodiment of the invention, a lesional biopsy site sampled by the FTSC device can be no larger than approximately 6 mm in diameter. In another embodiment of the invention, a lesional biopsy site sampled by the FTSC device can be no larger than approximately 10 mm in diameter. In an embodiment of the invention, a lesional biopsy site sampled by the FTSC device can be no larger than the diameter of the FTSC device head at a position 4 mm distal from the tip. In an alternative embodiment of the invention, a lesional biopsy site sampled by the FTSC device can be no larger than the diameter of the FTSC device head at a position 9 mm distal from the tip. In an embodiment of the invention, a lesional biopsy site sampled by the FTSC device can be no larger than a focal biopsy.

In an embodiment of the invention, lesions are accessible to an examiner during routine examination. In an alternative embodiment of the invention, lesions are not accessible to an examiner during routine examination. In another embodiment of the invention, access to lesions requires surgery. In an embodiment of the invention, the tissue surface to be sampled is accessible following entry into a body cavity through a natural orifice, canal, or surgical channel. In an embodiment of the invention, the tissue surface to be sampled is accessible following entry into a body cavity via a trochar using an endoscope with a biopsy port for inspection. In another embodiment of the invention, the tissue surface to be sampled is accessible following entry into a body cavity via a cannula. In another alternative embodiment of the invention, the tissue surface to be sampled is accessible following entry into a body cavity via an arthroscope, colonoscope, sigmoidoscope, sinus scope and anoscope.

In an embodiment of the present invention, the FTSC device head remains on the lesion due to the design of the device surface. In an embodiment of the present invention, the FTSC device head remains on the immediate area of intended biopsy/therapy due to the design of the device surface. In an embodiment of the present invention, the FTSC head has a facet with a fabric for functionally abrading epithelial surfaces including a backing material and a plurality of fenestrated loops attached to the backing material adhered to the facet. In an embodiment of the present invention, the FTSC head facet has a flat surface. In an alternative embodiment of the present invention, the FTSC head facet has a concave surface. In another alternative embodiment of the present invention, the FTSC head has a facet with a convex surface. The concave facet head allows a handle attached to the head to be rotated and ensures that the head remains on the desired location for convex tissue surfaces. The convex facet head allows a handle attached to the head to be rotated and ensures that the head remains on the desired location for concave tissue surfaces. The flat facet head with an adhered abrasive fabric allows the hand to be rotated and pressed completely without allowing gaps between the abrasion material and the surface tissue to be sampled when collecting a biopsy. In an embodiment of the invention, the head of the FTSC device is conical and pointed. In an embodiment of the invention, the head of the FTSC device is elliptical and pointed. In an embodiment of the invention, the head of the FTSC device is multifaceted and pointed.

An unexpected result that was observed during clinical trials of a number of FTSC devices, undertaken to test various prototype geometries, was that a pointed-tip rod enabled the clinician to more easily dilate the cervix, while not increasing the risk of damage to the cervix through an incision. In an embodiment of the invention, the diameter of the head of the FTSC device is a maximum of approximately 8 mm and tapers to a tip of less than approximately 1 mm. In an embodiment of the invention, the diameter of the head of the FTSC device is a maximum of approximately 5 mm and tapers to a tip of less than approximately 1 mm. In an embodiment of the invention, the diameter of the head of the FTSC device is a maximum of approximately 4 mm and tapers to a tip of less than approximately 0.8 mm. In an embodiment of the invention, the diameter of the head of the FTSC device is a maximum of approximately 3 mm and tapers to a tip of less than approximately 0.6 mm. In an embodiment of the invention, the diameter of the head of the FTSC device is a maximum of less than approximately 3 mm and tapers to a tip of less than approximately 0.6 mm.

An unexpected result observed during clinical trials was that an FTSC device with a maximum diameter of less than approximately 8 mm which tapered to a tip of less than approximately 1 mm enabled the clinician to insert the FTSC device into almost any cervical canal, and then gently press to insert the FTSC device further into the cervical os. In many cases, the insertion also dilated the cervix to allow entry of the device deeper into the canal. This is because the FTSC device head is a smooth tapered tip which acts like a dilator. That is because the distal approximately 10 mm (corresponding to approximately one-half the length of the facet) of the FTSC device head is a smooth tapered tip it acts like a dilator. That is because the distal approximately 13 mm (corresponding to approximately two-thirds the length of the facet) of the FTSC device head is a smooth tapered tip it acts like a dilator. It was unexpected that an FTSC device can be used to both dilate the cervical os and enter the cervix. It was also unexpected that the thinner pointed FTSC device did not significantly increase the risk of damage to the cervix by causing an incision or inadvertent puncture of collateral tissue.

In various embodiments of the invention, the pointed thin head of the FTSC device has one or more facet surfaces cut into the pointed tip to increase the area sampled in a longitudinal direction along the rod main axis. In an embodiment of the invention, the major axis of the facet surface is parallel with the major axis of the rod. In an embodiment of the invention, the minor axis of the facet surface is parallel with the major axis of the rod. In an embodiment of the invention, the one or more facet surfaces are at the distal end of the rod. In an embodiment of the invention, the widest portion of one or more of the one or more facet surfaces is at the distal end of the rod. In an alternative embodiment of the invention, the thinnest portion of one or more of the one or more facet surfaces is at the distal end of the rod. In an embodiment of the invention, one or more of the one or more facets have a concave surface. In an embodiment of the invention, one or more of the one or more facets have a convex surface.

In an embodiment of the invention, one or more of the one or more facet surfaces are diamond shaped. In an embodiment of the invention, one or more of the one or more facet surfaces are pear shaped. In an embodiment of the invention, one or more of the one or more facet surfaces are triangle shaped. In an embodiment of the invention, one or more of the one or more facet surfaces are hybrid triangle-pear-shape. In an embodiment of the invention, one or more of the one or more facet surfaces are hybrid diamond-pear-shape. The hybrid diamond-pear shaped facet surface with the diamond end distal to the handle enhances the pointed feature of the FTSC head, while the pear shaped end proximal to the handle increases surface area. Due to the tapered fit of the device into the canal orifice, the canal itself steadies the device as it is rotated, where pressure can be applied maximally to the fabric surface during rotation.

In an embodiment of the invention, the distal surface of the FTSC thin head has abrasive material attached. In an alternative embodiment of the invention, abrasive material is associated with the surface of the FTSC pointed thin head. In another embodiment of the invention, one facet surface of the FTSC pointed thin head has abrasive material adhered to the surface. In an embodiment of the invention, one or more of the one or more facet surfaces of the FTSC pointed thin head has abrasive material applied. In another alternative embodiment of the invention, two or more facet surfaces of the FTSC pointed thin head have abrasive material applied.

In an embodiment of the invention, the length of the facet on the FTSC device tip is approximately 19 mm long. In an embodiment of the invention, one or more of the one or more facet surfaces begins at the tip of the FTSC device head and extends towards the handle. In an embodiment of the invention, the diameter of the FTSC head 4 mm distal from the facet tip is approximately 2 mm. In an embodiment of the invention, the diameter of the head 9 mm distal from the facet tip is approximately 2.5 mm. In an embodiment of the invention, the diameter of the head 12 mm distal from the facet tip is 3 mm.

In an embodiment of the invention, the maximum overall diameter of a FTSC device with one facet is the sum of the maximum diameter of the head and the length of the abrasive material attached to the facet. In an embodiment of the invention, the overall diameter of a FTSC device at a point with one facet is the sum of the diameter of the head at that point and the length of the abrasive material attached to the facet.

In an embodiment of the invention, the abrasive material comprises loops that have a short hook end, wherein the distance from the top of the loop to the bottom of the hook is less than approximately 50% of the length of the loop. In an embodiment of the invention, the abrasive material comprises loops that are approximately 4 mm in length. In this embodiment of the invention, the maximum overall diameter of a FTSC device with maximum diameter 3 mm and one facet is 7 mm. In an embodiment of the invention, the abrasive material loops are approximately 3.5 mm in length. In this embodiment of the invention, the maximum overall diameter of a FTSC device with maximum diameter 3 mm and one facet is 6.5 mm.

In a FTSC device with maximum diameter 3 mm and with abrasive material comprising loops that are approximately 3 mm in length, if the distal 4 mm of the FTSC head is inserted then the FTSC device tip including the abrasive material has a diameter at this point (4 mm distal from the tip) of approximately 5 mm. In an embodiment of the invention, the diameter of the head greatly facilitates access into the cervical os. In this embodiment, the cervix needs be dilated less than approximately 5 mm in order for the distal 4 mm of the facet of the FTSC device to enter the cervical cavity. It has been found that some cervical os diameters are 1-2 mm at the entry point. In this embodiment, the cervix needs be dilated less than approximately 3 mm in order for the distal 4 mm of the facet of the FTSC device to enter the cervical cavity at the entry point with minimal bending of the abrasive material loops.

In another embodiment of the invention, a FTSC device with maximum diameter 3 mm and with abrasive material comprising loops that are approximately 3.5 mm in length, if the distal 4 mm of the FTSC head is inserted then the FTSC device tip including the abrasive material has a diameter at this point (4 mm distal from the tip) of approximately 5.5 mm. In this embodiment, the cervix needs be dilated less than approximately 3.5 mm in order for the distal 4 mm of the facet of the FTSC device to enter the cervical cavity. While the Kylon® material hooks deform and bend somewhat and can be squeezed down tightly with a very tight fit, they lose their ability to abrade if the hooks remain perpendicular, rather than parallel to the canal mucosal surface. The hooks are intentionally designed to be angular and face away from the mucosal surface, as not to penetrate or lacerate primarily, but to shear and frictionally abrade with rotational torque.

An unexpected event was noted when in-vitro post-hysterectomy cervical tissue was sampled with the prior art, Velcro® or similar fabric, and compared to the result obtained using the Kylon® fabric. Conventional hooked fabric such as Velcro® which is designed for optimal fastening to another material provides hooks that are fenestrated too close to the fabric backing not allowing the hook tips sufficient contact to cause abrasion in a biopsy setting. The Kylon® fabric with its longer hooks and more distally cut fenestrations did permit frictional abrasion and tissue buckling and fracture. The Kylon® fabric provided adequate tissue sample for processing, analysis, and diagnosis.

In an embodiment of the invention, once the thin tapered FTSC device is inserted into the cervix, only the distal 4 mm of the facet corresponding to three to five hooks of the Kylon® material need to be inside the canal to obtain sufficient material for a biopsy requiring fifteen (15) to fifty (50) copies of DNA. In an alternative embodiment of the invention, once the thin tapered FTSC device is inserted into the cervix, only the distal 9 mm of the facet corresponding to ten (10) to twenty (20) hooks need to be inside the canal to obtain material for a biopsy requiring approximately 100-200 copies of DNA. In another embodiment of the invention, once the thin tapered FTSC device is inserted into the cervix, only the distal 12 mm of the facet corresponding to thirty (30) to forty (40) hooks need to be inside the canal to obtain material for a biopsy requiring approximately 300-500 copies of DNA. Unlike conventional curettage, the FTSC head device can be rotated and the hooks will contact the os canal and frictionally abrade, circumferentially being pressed against the endocervical epithelium, while being pressed and rotated. Since the Kylon® material has a greater propensity to 'hold' the tissue, more tissue is available for pathological analysis. This improves the diagnostic probability of determining the causitive agent. Importantly, tissue yield is crucial when scanning pre-cancerous lesions.

In an unexpected result, a prototype FTSC cone-shaped device tip with no facet and a maximum overall diameter of 9 mm (maximum diameter of head was 3 mm extending to the tip of approximately 1 mm diameter) was found not to fit inside a number of stenotic os cavities even after dilation of the cervix. The prototype FTSC cone-shaped device tip was wrapped with Kylon® material applied 360 degrees around the device. This added approximately 6 mm (twice the length of the loops) to the maximum diameter of the head. The overall diameter at a point 4 mm distal from the tip was 8 mm. Similarly, the rectangular Kevorkian curette was found not to fit into most stenotic os cavities.

In an embodiment of the invention, the FTSC device head is a round or trumpet shaped cylinder. The facet can be flat, concave, or covex in shape. This provides one or more concave facet surfaces at the distal end of a disc or disc-like protrusion without a tapered end. The one or more concave surfaces allow the FTSC device to be placed on a specific location on a body surface, such as the exocervix, vagina, buccal mucosa, anal mucosa, perianal skin, or vulva and rotated without moving off the desired location. A convex sampling head best conforms to a concave tissue surface similar to a "lock in key" nature. A concave sampling head best conforms to a convex tissue surface similar to a "lock in key" nature. A flat tissue surface is best sampled by a flat sampling surface, eliminating gaps between the sampling surface and the epithelium. In an embodiment of the invention, the ability of the FTSC device to remain on a fixed location can allow improved sampling of epithelial tissue from the lesion. Because the FTSC device does not move off the lesion, it allows increased rotation of the FTSC device, which in turn ensures a frictional abrading to enable improved sampling. In contrast, other methods disclosed in prior art do not disclose, teach or suggest that the position from which the biopsy is sampled is to be visually located, guided and retained through the choice of the facet surface contour. The FTSC device captures surface and exfoliated cells through frictional abrading of the target tissue site without affecting the ability of the fabric hooks, arranged in rows which permit channels, to open and close, capturing and retaining tissue into those channels and the fabric body.

Figure 9A:
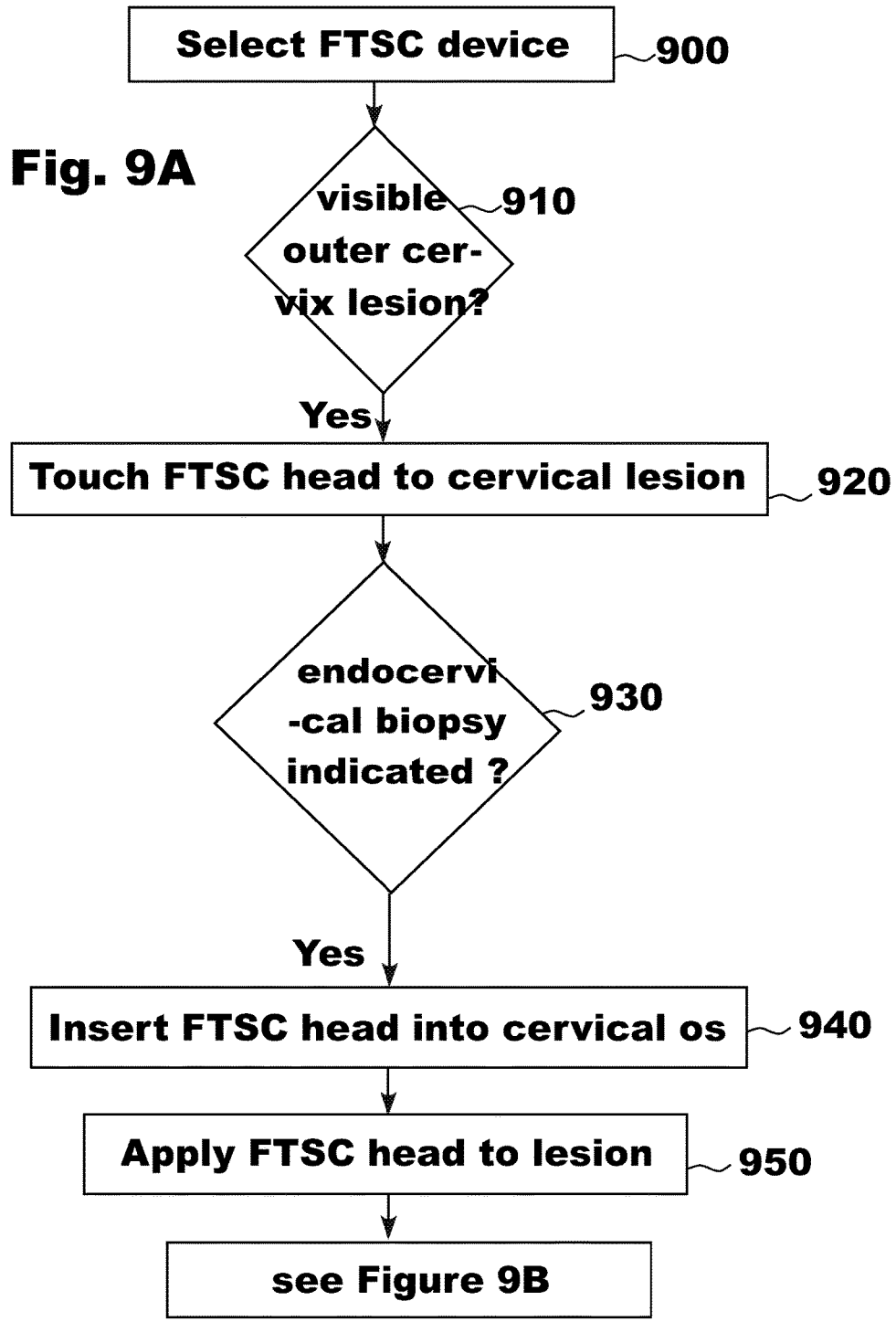
FIGS. 9(A) and (B) are flowcharts showing the use of the Frictional Tissue Sampling and Collection (FTSC) device used to take an endo-cervical biopsy sample in accordance with an embodiment of the invention.
Figure 9B:
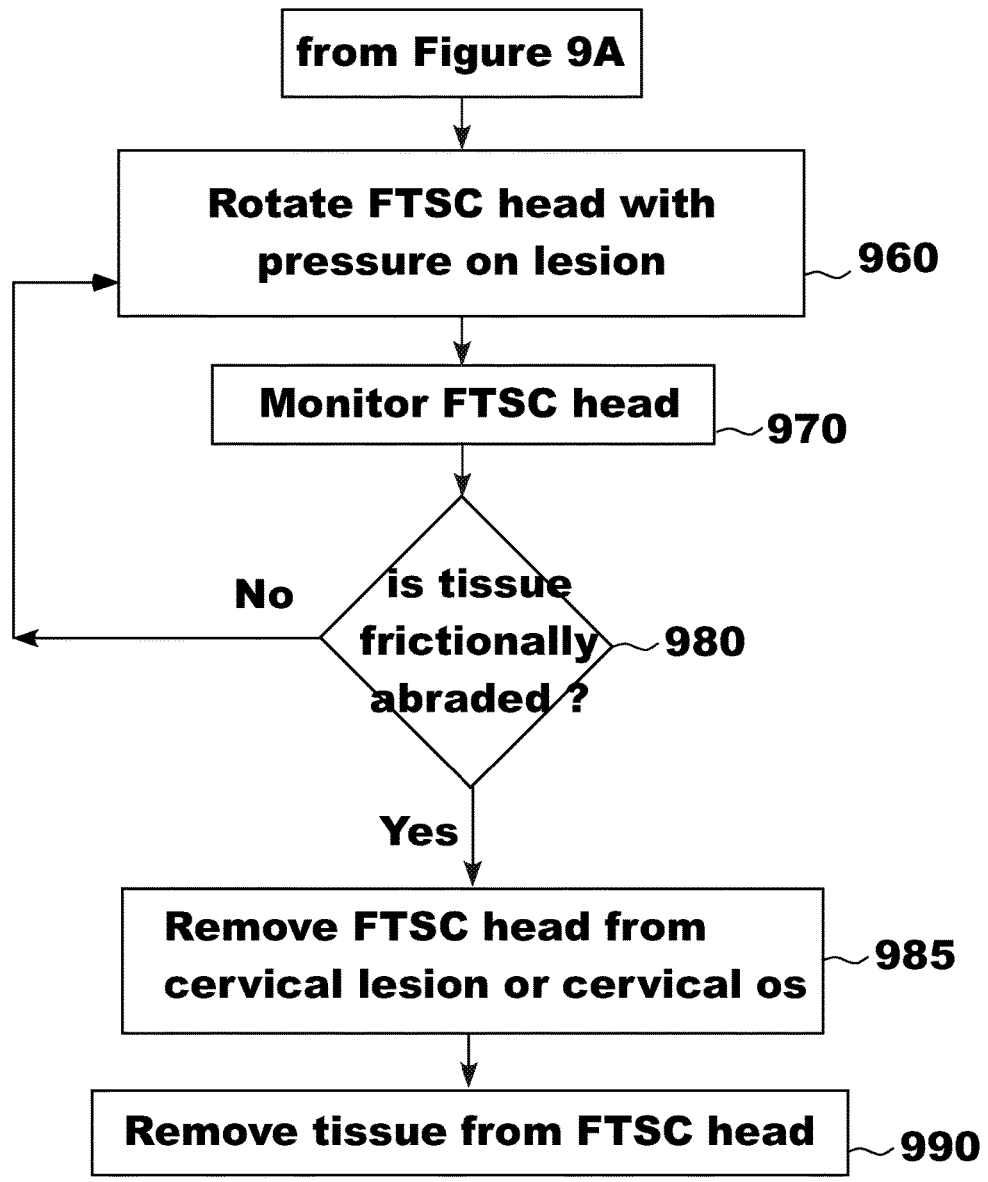

FIG. 9 shows a flowchart showing the use of the endo cervical FTSC device used to take a tissue sample from within the cervix in accordance with an embodiment of the invention. Initially a clinician selects an appropriate endo cervical FTSC head for device 900. The clinician touches the side of the FTSC head against the cervical opening 910. After the cervix opens, the FTSC head is inserted into the opening 920. The FTSC head can then be placed on the exposed lesion 930. The FTSC head can then be rotated 940. The clinician monitors the FTSC head 950 to determine when rotating the FTSC head has sufficiently frictionally abraded the lesion 960. The clinician then removes the FTSC head from the cervix 970. The tissue can then be removed from the FTSC head 980.

Figure 11A:
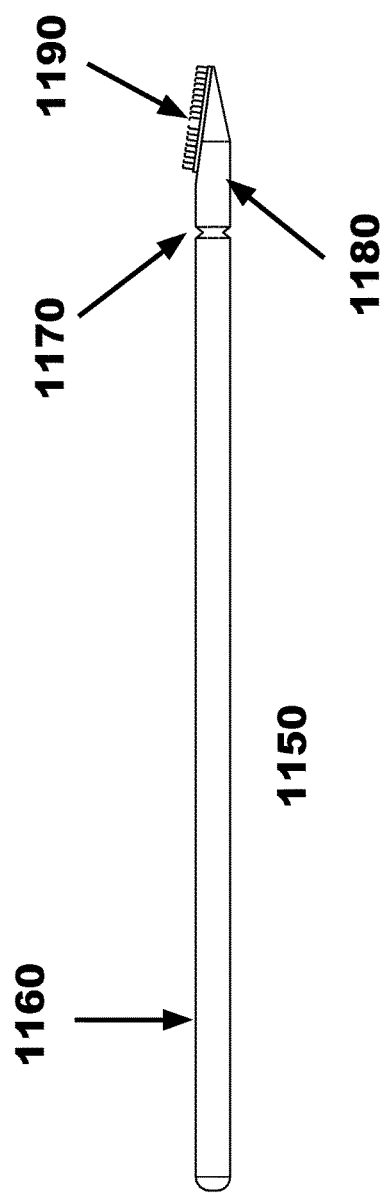
FIG. 11(A) is a schematic side view of an endo-cervical FTSC device in accordance with an embodiment of the invention.
Figure 12A:
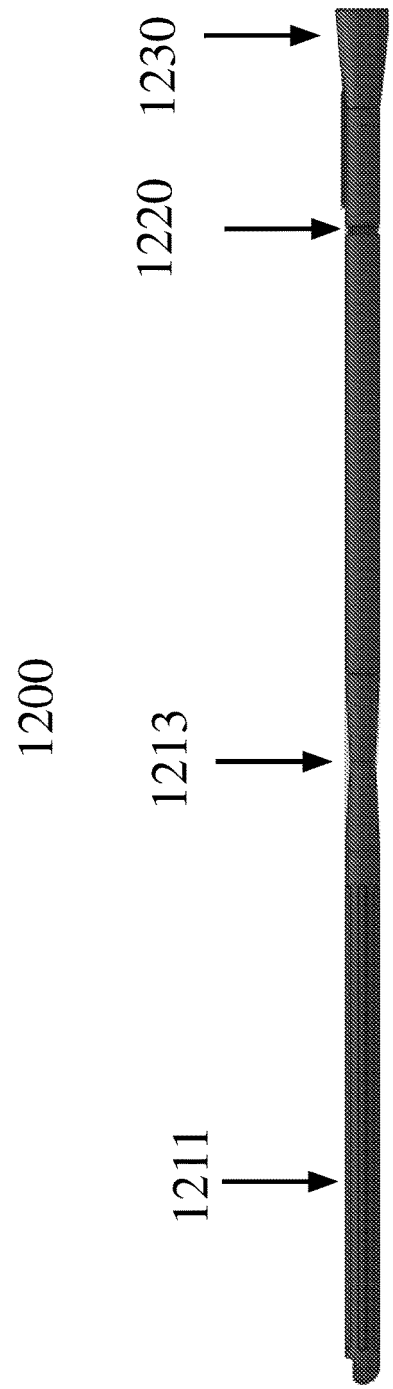
FIG. 12(A) is a schematic side view of an exo-cervical FTSC device in accordance with an embodiment of the invention.
Figure 12B:
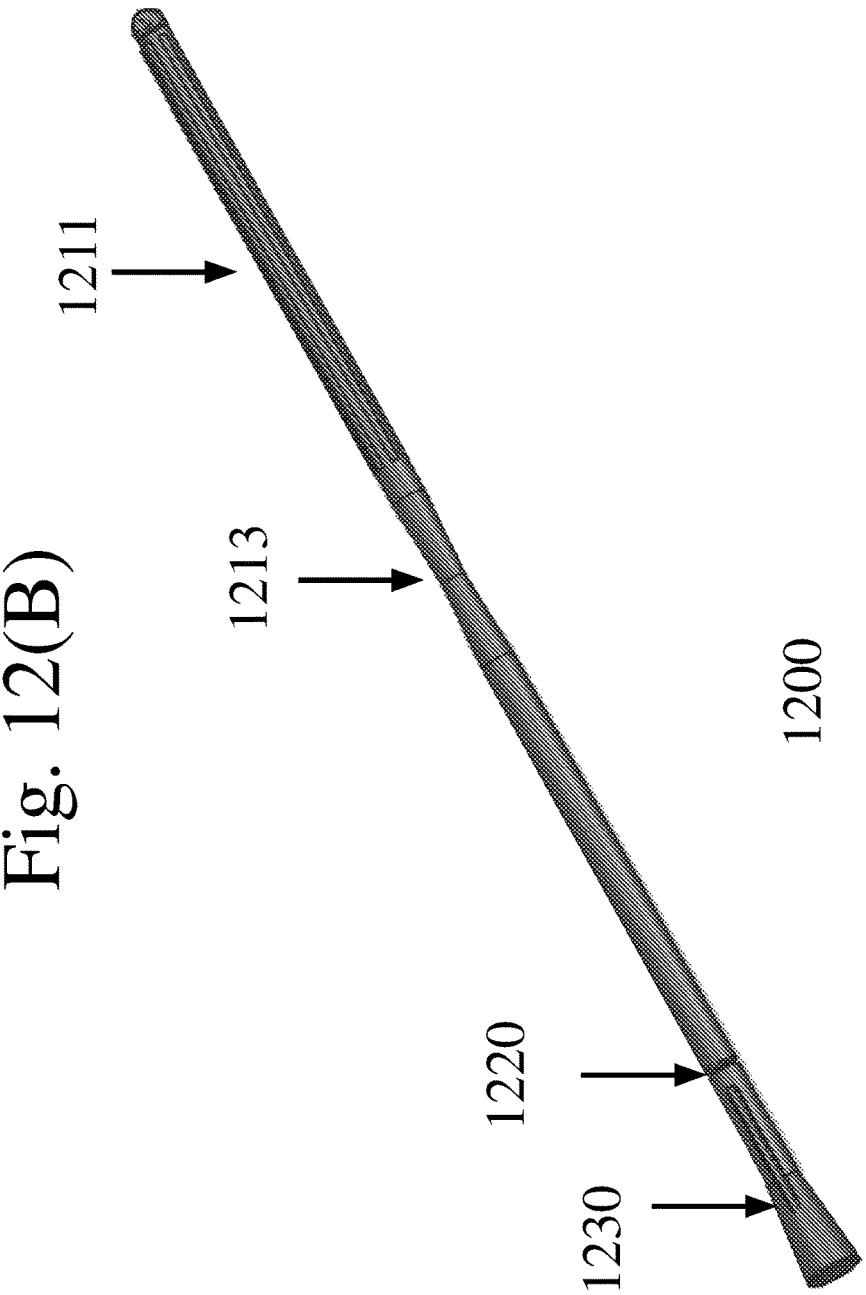
FIG. 12(B) is a schematic front view of an exo-cervical FTSC in accordance with an embodiment of the invention.
Figure 12C:
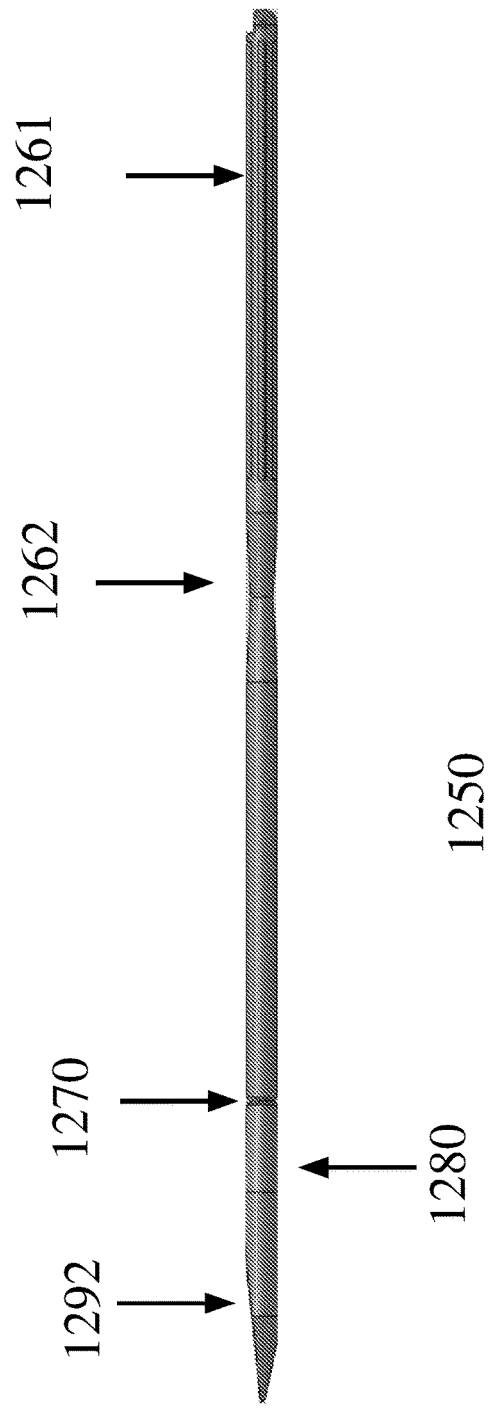
FIG. 12(C) is a schematic side view of an endo-cervical FTSC device showing a single facet in accordance with an embodiment of the invention.
Figure 12D:
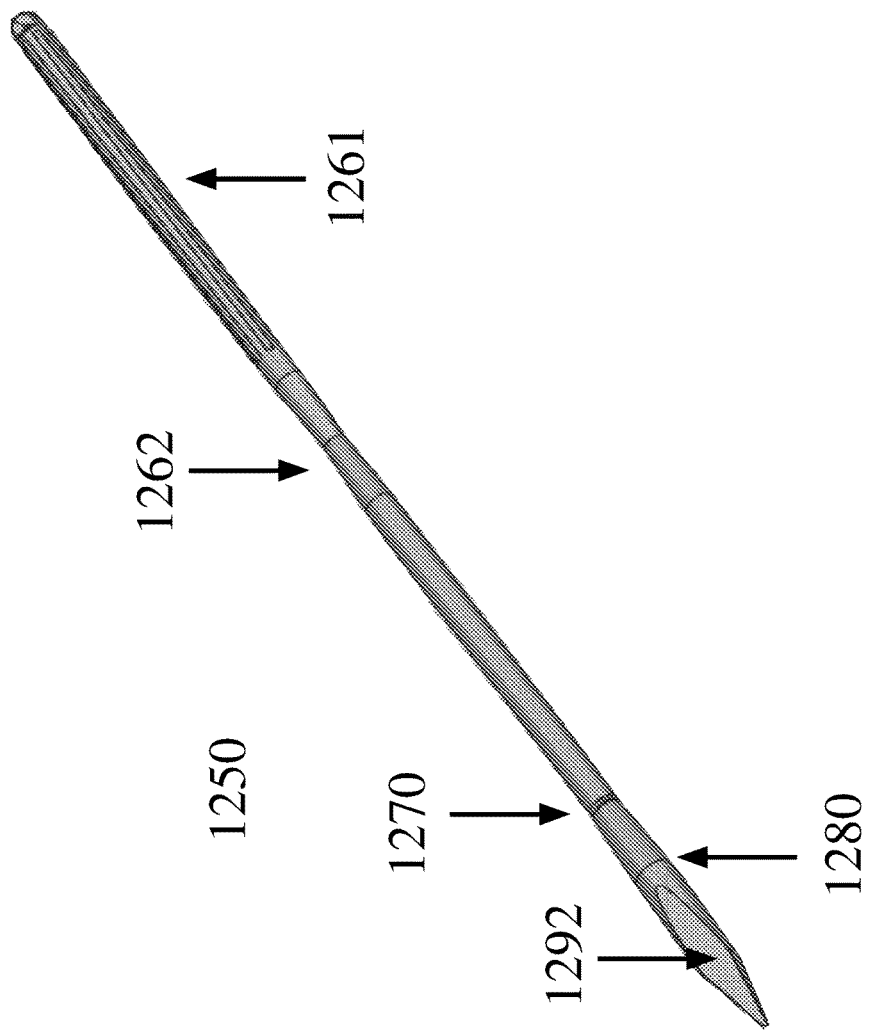
FIG. 12(D) is a schematic front view of an endo-cervical FTSC device showing a hybrid diamond-pear shaped facet in accordance with an embodiment of the invention.

FIG. 11(A) is a schematic side view of an endo cervical FTSC device 1150 showing the handle 1160 with an etched groove 1170 allowing for detachment, the head 1180 which has a single facet to which is adhered abrasion material 1190. The endo cervical FTSC device 1150 can be stored in a hematically sealed packet (not shown). FIG. 11(B) is an expanded side/frontal view of an endo cervical FTSC head showing the handle 1160 which has an etched groove 1170 allowing for the detachment of the head 1180, where the head 1180 has a single facet to which is adhered abrasion material 1190, in accordance with an embodiment of the invention.

Regional Biopsy

In various embodiments of the invention, the FTSC device can be used to biopsy and screen large geographic areas of tissue at risk for disease. In an embodiment of the invention, the FTSC device can be used to biopsy and screen neoplastic transformation such as, but not limited to, the squamo-columnar junction of the female cervix in the presence or absence of visualized lesions. In an embodiment of the invention, the FTSC device by providing one or more concave surfaces on an otherwise conical or rod-like protrusion, allows the device to be placed on a specific location and rotated without moving off the desired location. In an embodiment of the invention, the ability to remain on a fixed location can provide samples of epithelial tissue from specific locations for analysis. In this manner, the overall surface can be randomly sampled with a finite number of biopsy samples. In contrast, other methods disclosed in prior art do not allow the position from which the biopsy is to be sampled to be localized. The intent is to frictionally remove tissue from a variety of localized positions based on visual evidence of the larger area, or knowledge of the "at-risk" landmark area where disease is likely to evolve or be harbored, such as the "transformation zone" of the cervix, which can range from approximately 10-40 mm in diameter.

Simultaneous Biopsy of Epithelial Surfaces and Canal-Like Structures

In an embodiment of the invention, the surface of the head has abrasive material applied. In alternative embodiments, the device has a head with material applied that contains a central core of fenestrated loops that are longer (e.g., approximately 4-7 mm long), surrounded by a wider rim of shorter fenestrated loops (e.g., approximately 3 mm in length). The longer loops are geometrically suited to insinuate within a central canal structure, such as the endocervical canal of the cervix. There is simultaneously uniform contact of the fenestrated loop fibers circumferentially around the endocervical canal on the flat exocervical surface. With rotation and agitation in a back-and-forth motion using a brush, tissue can be used to harvest within the fenestrated loop channels. In an embodiment of the invention, the abrasive material can be the Kylon® material fabric. Because the tissue is held by the Kylon® material fabric, when the FTSC head is sent to the pathologist, the pathologist can require a tool to remove the tissue from the FTSC head. Unlike bristle brushes that are twisted, Kylon® material fabric hooks are arranged in rows. In contrast to Velcro® material, the hooks are shallow, and the fenstrations distal and narrow, thus the Kylon® can be combed, and the tissue collected in the biopsy can be combed out. In an embodiment of the invention, a miniature mustache comb can be used to remove the tissue from the Kylon® material fabric. The technician has to comb the tissue directly out from the Kylon® material fabric into the vial of liquid fixative. Then the vial of fixative containing the mixed tissue can be trapped on a filter paper. Alternatively, in an embodiment of the invention, the tissue can be teased free from the hooks of the Kylon® material fabric using a scalpel or tweezers. In an embodiment of the invention, the hooks of the Kylon® material fabric can be cut or sheared to remove the tissue from the fabric base for the biopsy. In an embodiment of the invention, the abrasive material can be dissolved in an appropriate solvent to remove the tissue from the abrasive material for the biopsy. In an embodiment of the invention, the tissue can be rinsed forcefully from the abrasive material on to the filter paper or collection vessel.

In an alternative embodiment of the invention, approximately 9 mm long central fibers are surrounded by approximately 3 mm fibers. In an embodiment of the invention, the device can be inserted into the cervix and rotated with spinning revolutions. Following frictional trans-epithelial tissue disruption, the head containing biopsy sample can be detached and inserted into a liquid vial of fixative.

Figure 10:
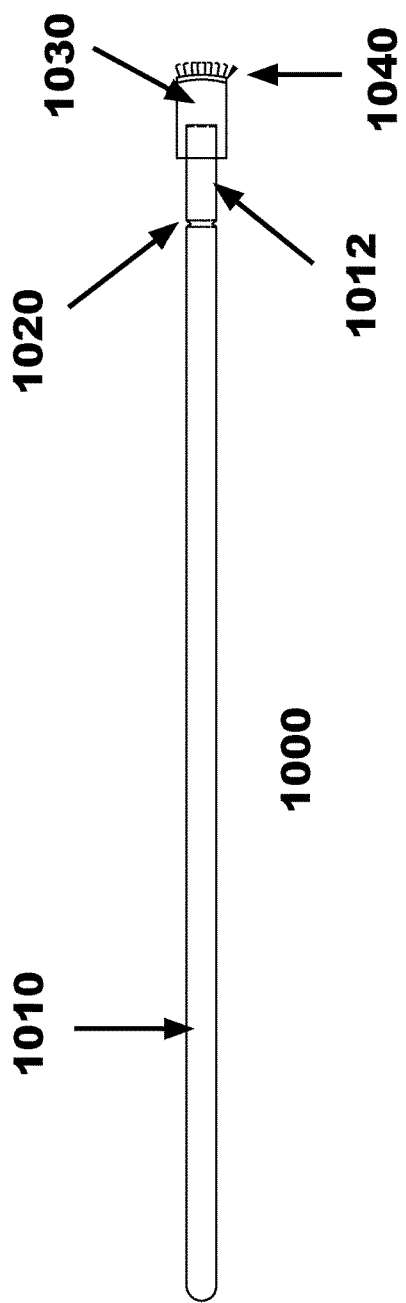
FIG. 10 is a schematic side view of an exo-cervical FTSC device in accordance with an embodiment of the invention.

FIG. 10 is a schematic side view of an exo cervical FTSC device 1000 showing the handle 1060 which has an etched groove 1020 allowing for the detachment of the head 1030, where the head 1030 which has abrasion material 1040 is adhered.

FIG. 12(A-D) are schematic views of endo- and exo-cervical FTSC devices, with ribbed handles and tapered waists. In FIGS. 12(A) and (B), the side view and front view of the endo-cervical device 1200 shows a ribbed handle 1211 and tapered waist 1213 which are designed to allow the clinician to easily and rapidly rotate the device 1200. The etched groove 1220 allowing for the detachment of the head 1230, is also shown. In FIGS. 12(C) and (D), the side view and front view of the exo-cervical device 1250 includes a ribbed handle 121 and tapered waist 12162 which are designed to allow the clinician to easily and rapidly rotate the device 1250. The etched groove 1270 allowing for the detachment of the head 1280, and the single hybrid diamond-pear shaped facet 1292 are also shown In an alternative embodiment of the invention, the FTSC device 1300 as shown in FIGS. 13A, 13B, 13F and 13H include a cylinder 1335 with a diameter of approximately 3 mm mounted on a disc 1330 with a diameter of 1.5 cm, which is connected to a handle 1310. In FIGS. 13A and 13H the disc 1330 is connected to the handle 1310 via a handle extension 1312 with a weakened portion 1320 to allow detaching of the disc 1330 from the handle 1310. In another alternative embodiment of the invention, a cylinder 1335 with a diameter of approximately 6 mm is mounted on a disc 1330 with a diameter of 3 cm, which is connected to a handle 1310. In FIG. 13A the disc 1330 is cylindrical, while in FIG. 13H the disc 1330 is cone shaped and the cylinder 1335 extending from the disc 1330 has a facet. FIGS. 13B and 13F show the face 1336 of the cylinder 1335, while FIG. 13A shows the cylinder 1335 is covered with abrasive fibers 1340. In Figure FIG. 13B the face is perpendicular to the main axis of the handle, while in FIG. 13F the face is at an acute angle to the main axis of the handle. In an embodiment of the invention, the face of the cylinder is covered with 3 mm long hooked Kylon® fibers. In an embodiment of the invention, the device can be inserted into the cervix and rotated with spinning revolutions. Following frictional transepithelial tissue disruption, the head containing biopsy sample can be detached and inserted into a liquid vial of fixative.

Figure 13C:
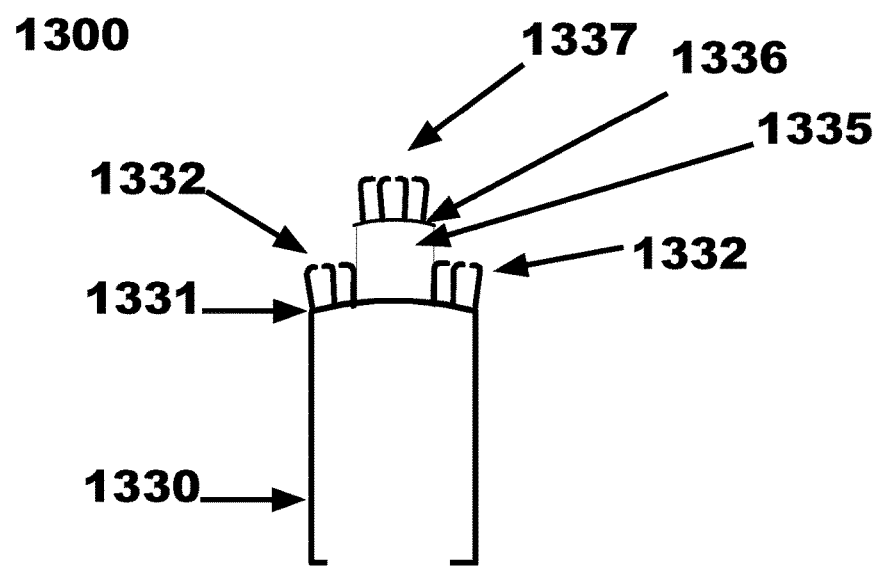
FIG. 13(C) is an expanded side view of an FTSC device with a cylinder extending from the distal surface of a disc as shown in FIG. 13(B) and the collection material attached on the distal surface of the disc and collection material attached to the distal surface of the cylinder in accordance with an embodiment of the invention.
Figure 13D:
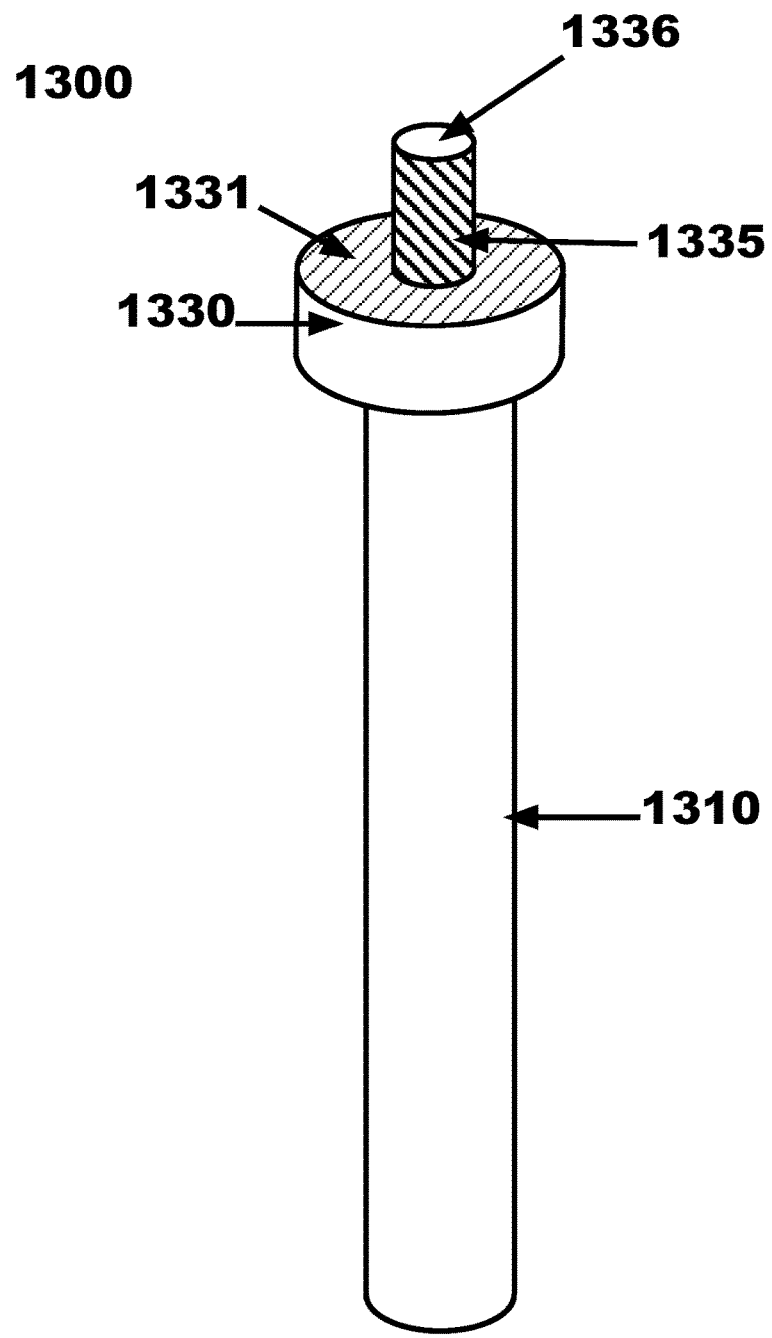
FIG. 13(D) is a side view of an FTSC device with an elongated cylinder extending from the distal surface of a disc in accordance with an embodiment of the invention and the disc connected to a handle.
Figure 13E:
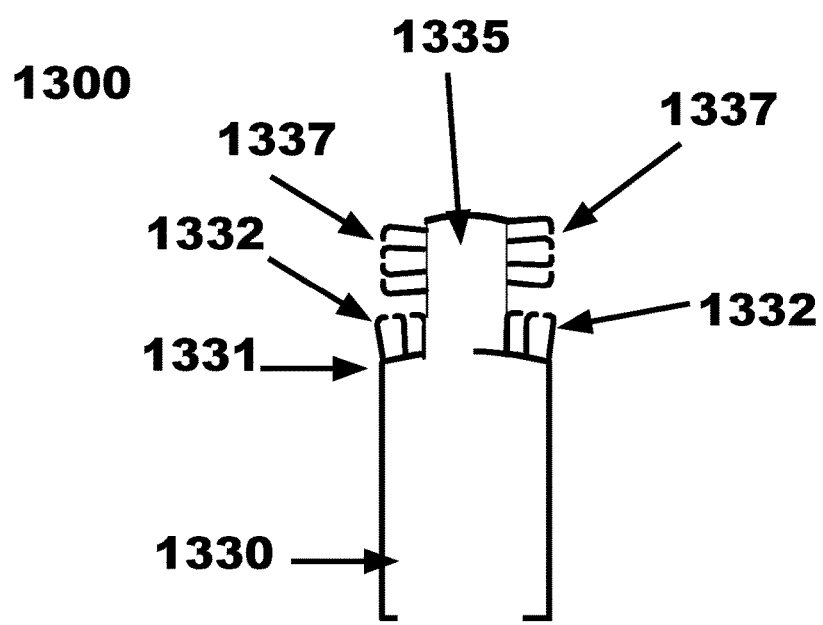
FIG. 13(E) is an expanded side view of an FTSC device with an elongated cylinder extending from the distal surface of a disc as shown in FIG. 13(D) and the collection material attached on the distal surface of the disc and the surface of the cylinder in accordance with an embodiment of the invention.
Figure 13F:
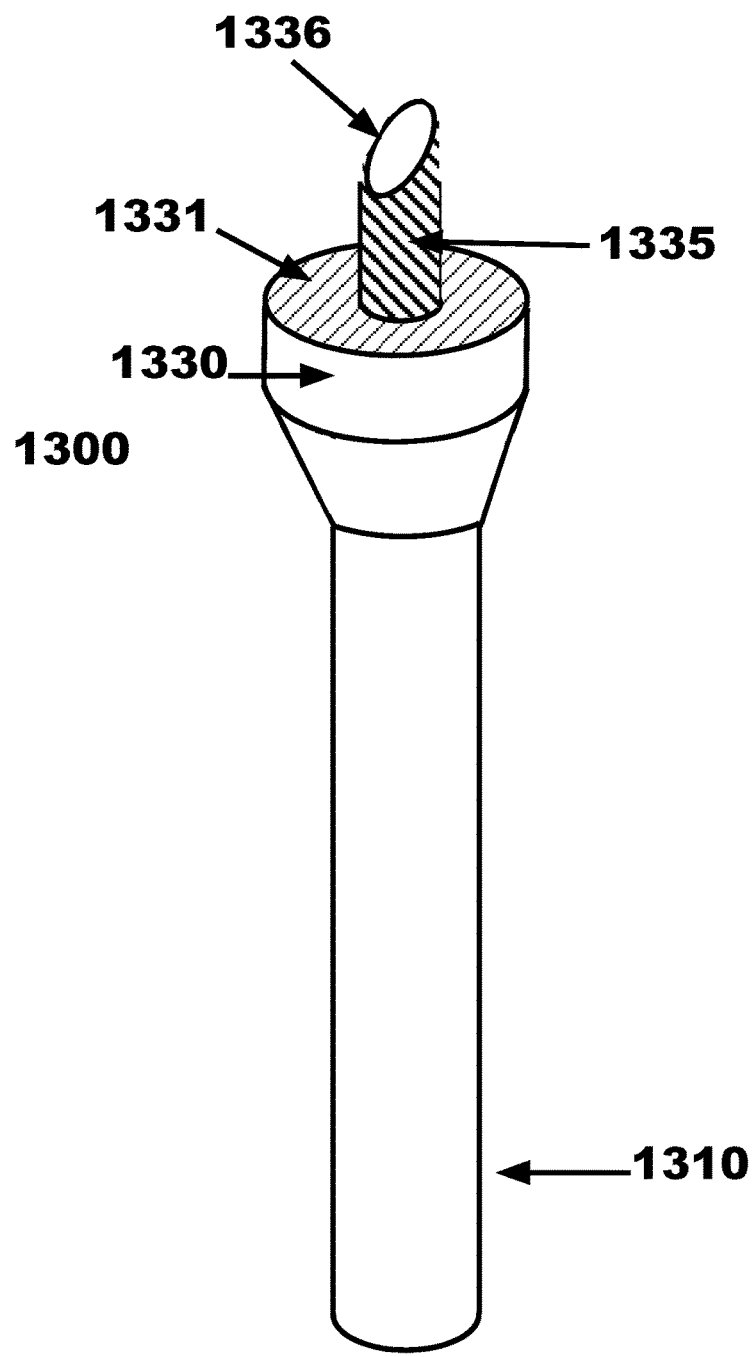
FIG. 13(F) is a side view of an FTSC device with a cylindrical facet extending from the distal surface of a disc and the disc connected to a handle in accordance with an embodiment of the invention.
Figure 13G:
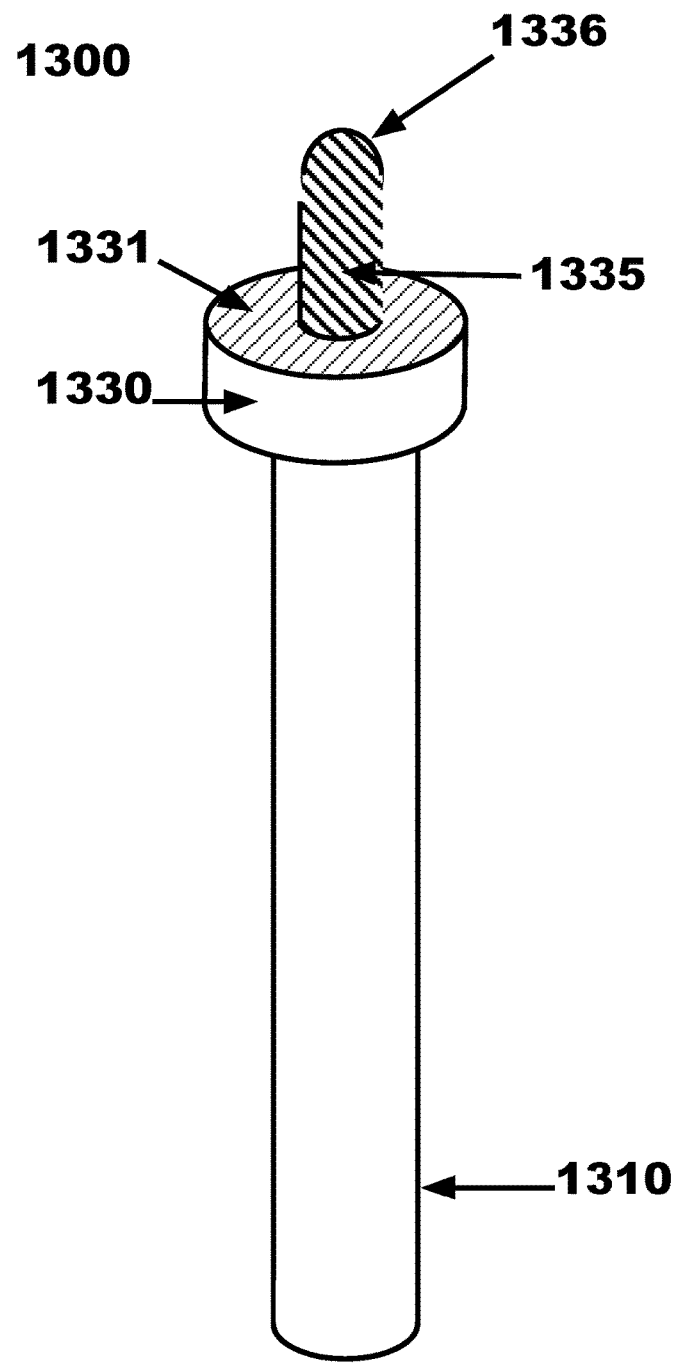
FIG. 13(G) is a side view of an FTSC device with an elongated cylinder with a rounded tip extending from the distal surface of a disc in accordance with an embodiment of the invention and the disc connected to a handle.
Figure 13J:
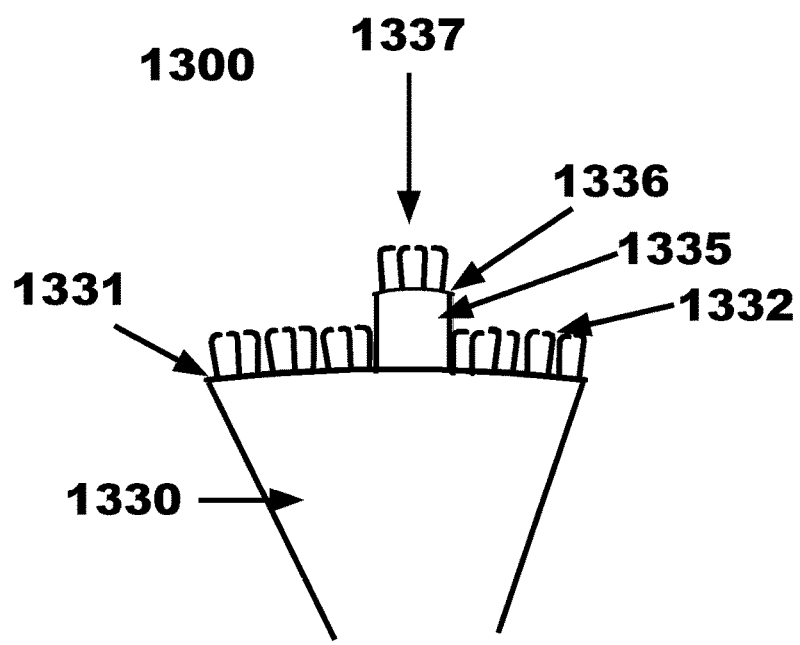
FIG. 13(J) is an expanded side view of an FTSC device with a cylinder extending from the distal surface of a cone shaped disc and the collection material attached on the distal surface of the cone shaped disc and collection material attached to the distal surface of the cylinder in accordance with an embodiment of the invention.

In alternative embodiment of the invention, as shown in FIGS. 13C and 13J, a cylinder 1335 or round faced trumpet designed tip with a diameter of approximately 3 mm is mounted on a disc 1330 with a diameter of 1.5 cm. In another embodiment of the invention, a cylinder 1335 with a diameter of approximately 6 mm is mounted on a disc 1330 with a diameter of 3 cm. FIG. 13D shows the face 1336 of the cylinder 1335 and the face 1331 of the disc 1330. FIG. 13G shows a rounded end 1336 of the cylinder 1335 and the face 1331 of the disc 1330. As shown in FIGS. 13C and 13J the face 1336 of the cylinder 1335 is covered with abrasive fibers 1337 and the face 1331 of the disc 1330 is also covered with abrasive fibers 1332. In FIG. 13C the disc is circular, while in FIG. 13J the disc is trapezoid. In an embodiment of the invention, the face of the cylinder is covered with 3 mm long hooked Kylon® fibers and the face of the disc is also covered with 3 mm long Kylon® fibers. In another alternative embodiment of the invention, as shown in FIG. 13E, the surface of the cylinder 1335 is covered with abrasive fibers 1337 and the face 1331 of the disc 1330 is also covered with abrasive fibers 1332. In an embodiment of the invention, the surface of the cylinder is covered with 3 mm long Kylon® fibers and the face of the disc is also covered with 3 mm long Kylon® fibers.

The clinician inserts the cylinder 1335 onto the exo-cervical tissue or lesion, and position the FTSC device disk surface 1331 flush with the exo-cervix. In an embodiment of the invention the cylinder surface 1336 can be flat. In an embodiment of the invention the cylinder surface 1336 can be concave. In this embodiment, a slight concave shape can be used to match the convex cervical contour. In an embodiment of the invention the cylinder surface 1336 can be convex. In this embodiment, a slight convex shape can be used to enhance fit into epithelial concave shaped areas. In an embodiment of the invention the disk surface 1331 can be flat. In an embodiment of the invention the disk surface 1331 can be concave. In an embodiment of the invention the disk surface 1331 can be convex. In an embodiment of the invention the disk surface 1331 can be at an inclined angle relative to the cylinder surface 1336. In an embodiment of the invention the disk surface 1331 can be inclined at an angle of 15° relative to the cylinder surface 1336. In an alternative embodiment of the invention the disk surface 1331 can be inclined at an angle of 30° relative to the cylinder surface 1336. In another alternative embodiment of the invention the disk surface 1331 can be inclined at an angle of 45° relative to the cylinder surface 1336. In another embodiment of the invention the disk surface 1331 can be inclined at an angle of 60° relative to the cylinder surface 1336. Once the cylinder 1336 is inserted and the disk surface 1331 is in contact with cervical tissue surface, it is pressed and rotated several revolutions clockwise and counterclockwise to obtain the biopsy sample. In this embodiment of the invention, the disk surface 1331 of the FTSC device is large enough to cover the entire "at risk" area of the cervix, commonly known as the "transformation zone" where cancer precursors and cancer is likely to develop/start. A concave cylinder surface 1336 can simultaneous dilate the cervix while the concave cylinder design ensures better contact with tissue.

Figure 14:
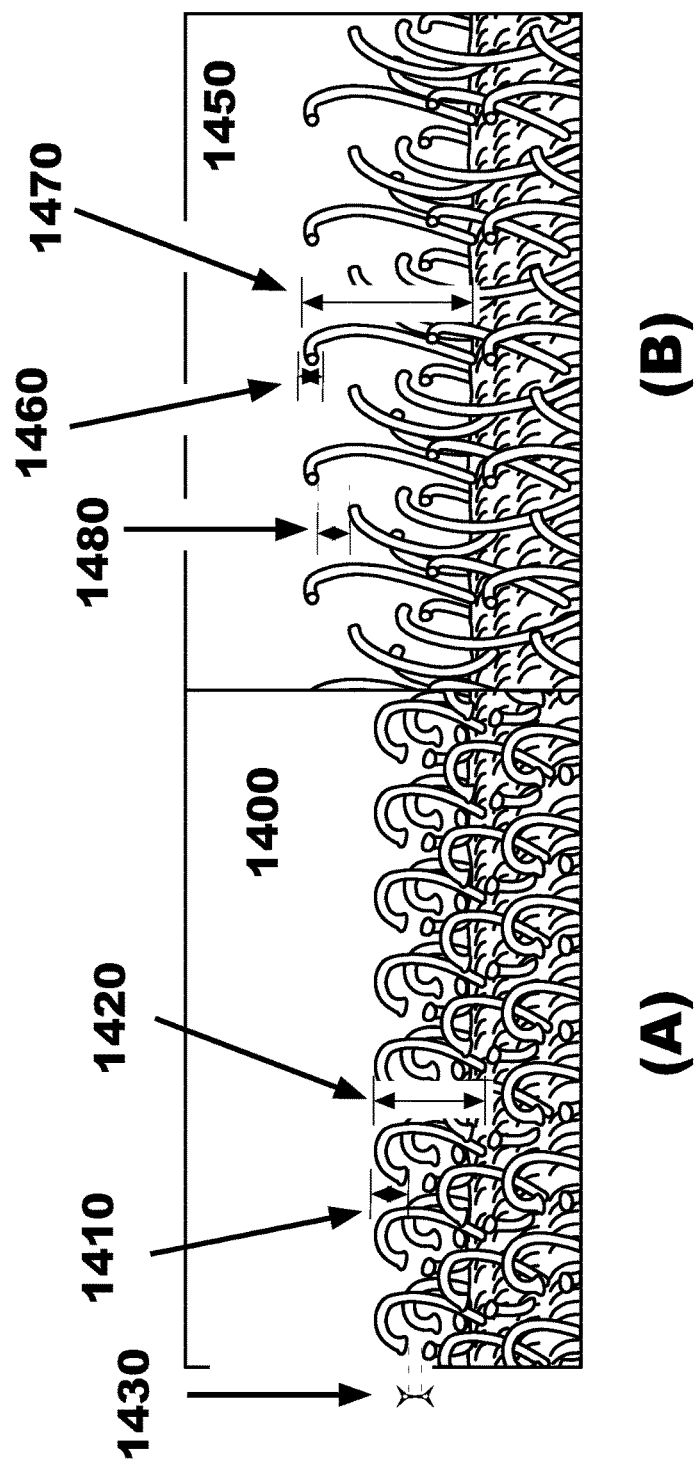
FIG. 14 is a schematic of an expanded side view of (A) 2 mm Velcro® and (B) 3.1 mm Kylon® material.

FIG. 14 shows a line drawing representative of a comparison of (A) 2 mm Velcro and (B) 3.1 mm Kylon material. The material 1400 shown in FIG. 14(A) has an arc 1410 which is more than approximately 25% of the length of the loop 1420 and a relatively narrow fenestration 1430 which is less than approximately 0.4 mm. The material 1450 shown in FIG. 14(B) has a narrow arc 1460 which is less than approximately 15% of the length of the loop 1470 and a relatively wide fenestration 1480 which is more than approximately 0.6 mm.

Frictional Tissue Sampling and Collection Biopsy Devices

In an embodiment of the invention, the frictional tissue sampling and collection biopsy devices disclosed herein utilize Kylon® material, a fabric that includes minute plastic (e.g., nylon) fiber loops that are fenestrated at a minimal distance from the apex of the loop. The loops flex but do not fracture under minimal to moderate force, or separate under pressure.

The semi-rigid loops can be pressed in a rotational manner (e.g., in sweeping or circular motion) away from or toward the clinician, perpendicular, or at an angle into epithelial tissue surfaces. The semi-rigid loops remain flexible enough to cause separation of the fenestrated ends, creating frictional forces sufficient to cause local heating and buckling of the epithelial surface away from the underlying stroma. The loops are fenestrated such that with applied pressure they are flexible enough to open and provide access to a "collection well" for histological fragments. The tips of the fiber hooks are oriented away from the tissue. On pressing and rotation across the tissue surface, the fibers scrape, buckle and shear the epithelium from the underlying stroma. The fragments are excoriated from the tissue surface through the concomitant application of frictional forces applied to the tissue surfaces by the fenestrated loops. The frictional forces overcome the adhesive and binding forces of the tissue below to release fragments of various shapes and size, all eligible for collection in a histology lab, and subsequent processing and analysis.

The semi-rigid loops (e.g., made of nylon) hold the tissue fragments after excoriation because the loops are elastic enough to sufficiently re-close and capture the removed tissue. In addition, the spaces between the fibers also retain excoriated tissue. The frictional forces exceed the binding forces afforded by adhesion molecules which anchor epithelia to the basement membrane, as well as disrupting Van der Waals forces.

Once the epithelium is frictionally sheared from the underlying stroma, the tissue clumps and epithelial fragments are swept and excavated by the distal most curved apex of the loop and entrapped within the geometrically suited spaces between the closed, fenestrated loops. Thus, the method is frictional abrasion, excavation via rotation and other directional motion, and tissue collection within inter-loop channels.

The Kylon® material fabric can be cut into uniform shapes such as a hybrid diamond-pear shape, a pear shape, a circular disc or straight edge shape(s) and with uniform height, allowing the device to provide 360-degree coverage of tissue surfaces over suspected lesions, without a gap within the circumference of the device. The Kylon® base material is also flexible to allow the material to be applied to a concave or covex surface. This is in distinction to bristle brushes which are spiral or bent in shape, which present surface gaps. This does not allow uniform contact with the target tissue, and gaps and spiral or irregular orientation to tissue, that when pressed, agitated, or rotated penetrate the tissue surface causing a traction point, which can cause migration of the device from the lesion site toward the direction of rotation when such devices are pressed onto lesions and rotated or moved for tissue harvesting.

Following biopsy, the head of the device is readily severed from the handle to allow the head to be deposited in a liquid fixative agent. In an embodiment of the invention, the handle material is scored (thus weakened) near the head to allow the head to be broken off from the handle and deposited in liquid fixative, which is usually formaldehyde or alcohol. The Kylon® material fabric, fibers, and/or device head (all with the tissue entrapped between the fibers) are removed from the vial of liquid fixative to remove the tissue from the head of the device and process it for analysis. Therefore, one may intentionally design the device in an embodiment in which the user can easily decouple the device head from the device shaft. For example, some embodiments can have the shaft inserted into the head via a clip or screw thread mechanism, a key-in-lock design with a pressure release button, or a luer-lock type of attachment. Once the biopsy is obtained, the head and handle/shaft parts can be decoupled, wherein the handle can be discarded, or sterilized and re-used, and the head immersed in a vial of fixative.

Some methods for removal of tissue from the fiber assembly include using a brush, rinsing under pressure, immersion and agitation manually or mechanically, or by sonication. Alternatively, the fibers can be sheared from the fabric on telfa or other filter paper, and the fibers plucked off the paper leaving the entire biopsy specimen. Alternatively, after tissue is collected into the device channels, tissue can be deposited via rotation or agitation in a vial of liquid fixative, rinsed off the device under pressurized spraying, or removed from the nylon fibers by cutting away the nylon fibers from the fabric (e.g., onto filter paper), thus leaving the tissue on the paper, which can be immersed in fixative.

In preferred embodiments, the Kylon® material fabric fibers are manufactured in a similar manner to Velcro® or other hook and pile type fastener, where strands are longer than conventional hook and pile, approximately 3 mm in length, can range between 3 mm and 9 mm in length, are fenestrated closer to the apex of the loop instead of close to the base of one arm of the loop, and thus appear V-wishbone shaped. They have a short hook end with the curvature starting at 2 mm from the base. Because the loop strands are longer, they flex and bend to a greater angle and twist with greater elasticity when rotated or agitated when compared with standard Velcro®. Because the fenestration is closer to the base in standard Velcro®, the loop fenestrations do not separate, leaving the curved smooth surface of the loop in contact with the tissue, and therefore not providing sufficient frictional forces during rotation to shear and separate the epithelium from the underlying basement membrane and stroma.

Preferred embodiments utilize minute plastic fenestrated loops that are pressed perpendicular or at an angle into epithelial tissue surfaces which, upon rotational or agitational pressure forces, cause tissue epithelial fragments to be frictionally separated from the underlying tissue basement membrane and stroma. The channels between the fenestrated loops entrap and collect the tissue fragments. The process is similar to curettage with a blunt curved tool, which also scrapes, shears and strips epithelium from the underlying stroma of target tissues. On the other hand, the process is in contrast to sharp curettage where the purposefully sharp edge of the curette first incises, pierces, then shaves and scoops epithelium and underlying stroma from the tissue surface. The process described herein is less perceptible to patients than conventional biopsies and causes a smaller amount of blood loss and trauma.

In an embodiment, the present invention relates to a frictional trans-epithelial tissue apparatus. In various embodiments, the apparatus comprises approximately 3 mm or smaller loops adherent to and projecting perpendicular from a surface, with a density of approximately 50-1000 loops per square inch, evenly spaced or arranged in rows. The loops can be intact or fenestrated at the center or at their lateral aspect to allow for added flexibility and constructed from plastic, metal, or another stiff material. The rounded end of the loop is opposite the surface.

Loops can be of sufficient flexibility to withstand frictional forces and not fracture, and of sufficient tensile strength to generate sufficient frictional shear force during a sweeping or circular motion of the device to remove epithelium from tissue. The space between loops can serve to capture and harbor the sampled tissue.

In various embodiments designed for focal lesional biopsy, a flat, flexible surface, which anchors the loops, can be approximately 10-15 mm, but is most practically approximately 5-10 mm in diameter and circular in shape. In alternative embodiments of the present invention, a concave surface anchors the Kylon® material loops. The shape can be another geometrical design if it affords an advantage in covering the target tissue area for sampling. The head can be hinged in such a way that it can be folded or compressed, inserted through a small endoscopic channel, and then reinstated to its original state with a sampling surface. It can be comprised of plastic, cloth, or another composite material. The loops can be threaded through and project away from the head towards the tissue surface. In various embodiments of the present invention, a hub fiber or "pin" that penetrates and anchors the center of the disc on the target biopsy area, can serve as a central post to rotate the disc around for stability.

In other embodiments intended to screen larger, regional tissue sites at risk for neoplastic transformation or other disease process, the shape can be circular, where the diameter can range from approximately 10-50 mm, and the loops can project at varied distances from the head towards the tissue surface. For the purpose of histological screening to detect cervical neoplasia, the central approximately 5 mm diameter disc projects longer (approximately 5-25 mm) fenestrated loop fibers, and can be surrounded circumferentially by the aforementioned approximately 3-23 mm long loop fibers. The longer fibers can insinuate inside canal structures, (e.g., the endocervical canal) simultaneously with contact of the shorter fibers with an outer endothelial surface (e.g., the exocervical surface). Upon pressure and rotation or agitation, the endocervical and exocervical tissues can be simultaneously frictionally sheared and collected. Histological screening can be necessary to correctly reflect the presence or absence of epithelial pathology, because adhesion molecules can prevent representative exfoliation from diseased tissue in some cases, leaving cytological screening methods lacking in accuracy. (see for example Lonky et al., J Low Genit Tract Dis. (2004) 8:285 "False-negative hybrid capture II results related to altered adhesion molecule distribution in women with atypical squamous cells pap smear results and tissue-based human papillomavirus-positive high-grade cervical intraepithelial neoplasia" and Felix et al., Am J Obstet Gynecol. (2002) 186:1308, "Aberrant expression of E-cadherin in cervical intraepithelial neoplasia correlates with a false-negative Papanicolaou smear").

Preferably, a frictional trans-epithelial biopsy sample is taken from a lesion or an anatomical region that is predisposed to disease.

In various embodiments of the present invention, the device includes a plastic, metal, or mixed composition disk or curved convex head, which provides a flat surface for a cylinder to be attached. The disk can be equal or greater in diameter than the cylinder. The disk is approximately 5-10 mm in length while the flat, concave or convex cylinder is less than approximately 3 mm in thickness.

In various embodiments of the present invention, the applicator probe can be comprised of a rod or cylindrical shape including any suitable material (e.g., wood, glass, plastic, paper or metal), which has the base, surface and loop unit at its most distal end, wherein the applicator probe is approximately 2-5 mm in diameter and approximately 15-30 cm in length. It is constructed larger or smaller depending on the access to the tissue surface. The shaft of the rod or cylindrical shaped applicator probe can be rigid or semi-rigid so as to not bow or arc when pressure is transmitted from the handle to the device head.

A handle into which the applicator probe can be transfixed is optionally mechanical, providing motorized rotational, drill-like movement or agitating vibration.

The device handle can be composed of stiff material, preferably plastic similar to Lucite, clear or opaque in coloration, rigid nylon plastic, or alternatively can be glass, wood or metal. The device head can take a variety of shapes, cylindrical or tapered in design, but the distal most surface face is circular, square, or polygonal, and can be composed of plastic (e.g., nylon). The device head diameter can range from approximately 5-50 mm. The abrasive material fabric can be welded to the nylon surface ultrasonically, or can alternatively be attached via adhesive, or via a rim or collar (e.g., which snaps on to the surface into a recess in the head of the device).

In some embodiments, the clinician examines tissue surfaces and chooses an area to be sampled based on the presence of a suspicious lesion. In other embodiments, the clinician chooses an anatomical landmark known to be "at risk" for neoplastic or disease transformation for the purposes of sampling the entire chosen surface. The new learning is that a deeper trans-epithelial biopsy grade sample can be obtained with a minimally invasive approach with minor discomfort or trauma. Thus far, in 15 cases in a prospective clinical trial, patients report the biopsy procedure using Kylon® biopsy material on the described applicator(s) induces little or no discomfort, with minor bleeding graded less than conventional curette or sharp biopsy devices.

The handle or applicator probe is grasped at its proximal end or handle. The distal portion or head of the device contains the base, surface and loops that project perpendicular from the base towards the tissue surface with the more rounded ends that are pressed against the tissue surface.

With moderate pressure, the examiner simultaneously presses and rotates the device against the tissue several times in a clockwise or counterclockwise direction, or agitating motion in alternating 75-120 degree rotations, clockwise and counter clockwise. These actions cause an opening or separating the fenestrated loops, thus performing frictional disruption of the tissue surface. Alternatively, a sweeping motion can be used. If a motorized handle is used, it can be activated to assist in the rotation or vibration of the device.

The harvested tissue is collected from the tissue surface, and some tissue already trapped in the loops themselves can be inspected and can be teased from the loops, or the loops transected from the fabric and separated, and the remaining tissue placed in a fixative solution.

As shown in FIG. 1, fabric with fenestrated loops (1) is connected to platform (2), which is in communication with head (3), located at a distal end of handle (5), optionally including an elongated rod (4). Referring to FIG. 3A, moderate force (8) is applied against a tissue surface (7). The device head is rotated (9) on the surface to frictionally separate or agitate the surface epithelium. The device head is rinsed or placed with tissue in the loops into fixative for subsequent pathological analysis.

An apparatus with a conical platform is depicted in FIG. 2. In FIG. 2A, fabric with fenestrated loops (1) is connected to conical platform (6). Referring to FIG. 3B, an apparatus with a conical platform can be inserted into a canal or cavity. The device head is rotated (9) while maintaining pressure force in direction (8). The device head with tissue in the loops is rinsed, combed or teased free, or placed into pathological fixative.

An apparatus with a motor configured to rotate the platform is depicted in FIG. 4. Fabric with fenestrated loops (1) is attached to platform (2) on head (3) at the distal end of an elongated rod (4), which is attached to a motorized handle (5).

In some embodiments, the head is detachable from the elongated rod/handle. Referring to FIG. 5, a detachable head configuration allows the distal portion with head (3), platform (2), together with attached fabric containing loops, to be detached and placed into a preservative medium for later tissue removal and pathological processing. Some embodiments can have the shaft inserted into the head via a clip or screw thread mechanism, or a luer-lock type of attachment (23). Tissue fragments that remain attached to the detachable head are in addition to any free tissue obtained and collected from the tissue surface or the device as a result of the frictional tissue sampling.

Referring to FIG. 6, epithelial tissue samples are obtained by frictional transepithelial tissue disruption. A representation of tissue with a squamous epithelial lined surface is depicted in panel (A). The squamous epithelial multilayer (11) is shown with superficial flat and basal cuboidal epithelium. Basement membrane (12) separates the squamous epithelial multilayer from the subcutaneous tissue stroma (13) and the underlying sub-stromal tissue (14). FIG. 6B depicts application of the frictional biopsy device to the tissue surface. The device head (3) is applied (24) to a chosen area where curved portions of the fenestrated loops (1) press against the epithelial surface. A representation of two abutting hooks is shown, creating a collection channel. A shorter arm (15), adjacent to the fenestrated loop (1), can remain following severing of an initial continuous loop to create the fenestrated loop. In FIG. 6C, simultaneous pressure, agitational, and rotational force (16) splays and separates the hooks/loops. Frictional abrasive forces create heat which buckles the epithelial surface. Referring to FIG. 6D, sufficient abrasion creates shearing and fracture of the epithelial surface at varying depths which could include fracture through the basement membrane into the subcutaneous layer. As shown in FIG. 6E, the hooks insinuate into the fracture plane, and with additional abrasive forces continue to shear the tissue fragments, while simultaneously retaining the tissue for capture and collection. At the completion of the biopsy process (FIG. 6F), the collection of hooks arranged in rows creates channels that collect and sequester the tissue and cell cluster fragments within the channels. When the device is removed from the epithelial surface, additional sample collection is achieved due to the flexibility and recoil of the hooks.

Referring to FIG. 7A, frictional trans-epithelial tissue disruption with a focal biopsy apparatus is shown at the outer lip of the exocervix (17), alternatively known as the "transformation zone" of the cervix (18). In this configuration, fenestrated loops (1) approximately 3 mm in length are used to disrupt and collect tissue fragments. FIG. 7B depicts an enlarged focal biopsy apparatus, with an enlarged view of fenestrated loops (1) attached to platform (2).

Referring to FIG. 8A, simultaneous trans-epithelial biopsy of epithelial surfaces and canal-like surfaces, in particular, biopsy of the endocervical canal (20) and the exocervical area around the endocervical canal (i.e., the transformation zone), is shown (19). Referring to FIG. 8B, a central core of elongated loops of approximately 5-25 mm in length (21) are surrounded by a wider rim of shorter fenestrated loops of approximately 3-23 mm in length (22).

The frictional tissue sampling and collection device can be used on any body surface, both external to the body, body cavities, or on internal organs. To access epithelial surfaces of internal body organs, the device head can be deflated, folded or collapsed to pass through a small aperture or port, and re-opened or expanded to fully expose the fabric to the biopsy surface. This device can be used on humans or any other living organism with an epithelial surface. Any tissue surface can be sampled. The ease of use in each case will be related to the strength of the individual tissue adhesion and binding forces in specific locations. The loops themselves can harvest the tissue and also serve as tissue collection reservoirs for later storage once placed in a fixative medium. The platform with the loops can be detached from any applicator for later examination and processing (i.e., decoupled from the instrument used to press against tissue surfaces to obtain the tissue sample).

If the tissue surface is a canal or concave shaped area of the body, instead of a perpendicular platform design, the loops are directly attached to the probe itself, which is gradually tapered at the end to facilitate insertion into the canal. The loops project perpendicularly from the probe surface at its distal end, and the unit, once placed into the canal that is lined on its surface with epithelium, contacts such epithelium snugly.

The loops can be mounted on the platform or project from the rim surface of the platform, perpendicular or at an angle to the platform along the margin of the platform, or attached to other delivery applicators, including the examiner's gloved finger, or other surgical instruments. The platform can be any shape or size which can fit on a tissue surface. The base assembly can be any shape or size, and can be permanently rigid or collapsible.

If the tissue surface lies within a canal-shaped tissue surface, the loops can be attached directly to the applicator probe, which can be inserted into the canal-shaped body cavity. The probe with the loops projecting from the surface and contacting the epithelium is rotated, causing the frictional disruption sampling from the tissue surface. The shape of the probe can be constructed in any shape that allows a snug fit into the canal. The loops can be arranged in rows or equally spaced, allowing for maximal contact and tissue collection.

Some embodiments of the invention comprise a motorized mechanical assistance via a mechanical handle into which the most proximal end of the applicator probe is inserted. Such mechanical assistance can enhance the rotational or vibratory force that the device transmits to the tissue after contact is established. This can increase the frictional forces and the speed of the tissue disruption/sampling and shorten the procedure time.

Preferred Parameters of Fibers

The frictional sampling loops of the invention are collectively referred to as fenestrated loop fibers. In particularly preferred embodiments, the fibers are made using the hooked side of a modified Velcro® or other hook and pile type fastener, where the strands are approximately 3 mm in length and are V-wishbone shaped. They have a short hook end with the curvature starting at approximately 2 mm from the base. In various embodiments, the loops can be approximately 2.5-25 mm in length, approximately 3-5 mm in length, approximately 3-10 mm in length, approximately 3-15 mm in length, approximately 3-20 mm in length or approximately 3-25 mm in length.

In comparison, standard Velcro® is approximately 2 mm long and is more hooked. Thus, the loops of the present invention are longer than those of standard Velcro®, they are made of a similar nylon material compared with standard Velcro®, are more flexible when rubbed on a tissue surface due to their length, and they have shorter loops that hook nearer to the end of the strands. In particular, the distance from the top of the loop to the bottom of the hook is preferably less than 50% of the length of the loop, more preferably less than 40%, still more preferably less than 30%, and even more preferably less than 20% the length of the loop. This distance is also preferably at least 1% the length of the loop, more preferably at least 5% the length of the loop, and still more preferably at least 10% the length of the loop. A case series of three post-hysterectomy samples proved that conventional hooked fabric such as Velcro® mounted on sampling devices, pressed and rotated on the cervical epithelial surface were incapable of harvesting tissue for biopsy, while the re-engineered Kylon® fabric frictionally abraded tissue to a trans-epithelial depth.

Thus, the invention includes hooks in all of the ranges between any of the preferred minimum distances and any of the preferred maximum distances. The bottoms of the hooks are preferably arranged so that they are all approximately the same distance from the loop, although this is not strictly necessary. Because the hooks are cut at a relatively distal location, the ends of the hooks are more accessible to the tissue surface allowing for uniform transmission of frictional forces to the tissue surface. As a result, the action of the fibers more effectively buckle and shear the tissue, while the loops sweep over and capture the tissue.

In a preferred embodiment, the loop fibers are arranged so as to efficiently capture tissue. Thus, in one preferred embodiment, the fibers are arranged in an orderly orientation. For example, the fibers can be arranged in rows between which the tissue can be captured. The hooks can be arranged to be oriented at approximately the same angle and direction in each of the fibers. Thus, the fibers can be organized such they all have a consistent direction and angle of orientation. In addition, the spacing between each of the fibers can be made to be the same or different.

In use, the device can be oriented so that the fibers are perpendicular to tissue, and then pressure is applied. As a result, the epithelial surface is frictionally sheared. Thus, the fibers are preferably mounted on a flat or curved platform, optimally 4-10 mm in diameter so as optimize this process. However, alternatively shaped platforms can also be used in certain embodiments. Because the fibers can be mounted directly on the platform, which can be flat or slightly curved, the orientation remains evenly spaced and the spaces inside the fenestrated loops and between them remain evenly distributed to facilitate tissue capture.

In some embodiments the platform can be in the form of a thumbtack, wherein it is attached to the handle. However, the platform and handle can take on a variety of forms. It is envisioned that the handle and the platform can be molded as one piece, and the fibers (e.g., modified Velcro® can be attached with adhesive or via ultrasonic or thermal welding of the fabric to the platform.

In an embodiment of the invention, the abrasive fabric can be attached or sewed into another fabric or material such as the finger of a glove, with the human finger or hand functioning as the applicator to frictionally press and abrade the tissue surface.

In an embodiment of the invention, the Kylon® fabric can be applied to existing surgical instruments such as a body part probe, clamp, or tissue manipulator via an adhesive. In this manner, the surgical instrument to which the Kylon® fabric is adapted serves as a biopsy collection device.

In an embodiment of the invention, the abrasive fabric can be derivatized with functional groups to bind specific marker molecules present on cells of interest. PCT Application Number: PCT/US2009/053944, titled "Porous Materials for Biological Sample Collection" to Zenhausern et al, which is incorporated by reference in its entirety, describes an inorganic material which can be used as the abrasive material rather than for example the Nylon which is used in Velcro® to allow the specific binding and/or the solubilization of the abrasive material with appropriate solvents.

Method of Inducing an Immune Response by Autoinoculation

In some embodiments, the trans-epithelial, frictional tissue sampling and collection devices described herein are utilized to agitate and disrupt epithelial cells containing a pathogen, or cellular proteins altered by a pathogen, to induce an immune response against the pathogen. This results in auto-inoculation of tissues that harbor pathogens and macromolecules such as virally altered DNA and/or oncogenic proteins. The method can also be termed therapeutic frictional abrasion-excoriation. This method is advantageous when a pathogen is normally able to evade an immune response. For example, some viruses remain in surface epithelial layers where they are sequestered from the immune system. Other viruses can be integrated into cellular DNA, thereby evading immune detection.

The methods of inducing an immune response against a pathogen that normally evades the immune system comprise the steps of (a) disrupting epithelial cells containing the pathogen, virally altered DNA, or cellular oncoproteins with a micro-curettage device described herein, and (b) introducing the pathogen into the bloodstream of a patient to elicit an immune response.

In some embodiments, the trans-epithelial, frictional tissue sampling and collection devices described herein are utilized to disrupt epithelial cells to induce an immune response against human papillomaviruses (HPVs). HPVs are persistent viruses that can remain in their hosts for long periods of time before causing any ill effects. Generally, the host reacts to viral pathogens by generating both humoral and cell-mediated responses. Humoral responses are typically antibody-mediated and involve the secretion of antibodies such as immunoglobulin A (IgA) and immunoglobulin G (IgG) by B lymphocytes. Cellmediated responses, on the other hand, are carried out by immune effector cells such as dendritic cells (DCs), natural killer (NK) cells, macrophages and T lymphocytes which secrete a number of cytokines including interferon (INF) and tumor necrosis factor (TNF), and up-regulate the expression of Fas ligand (FasL) and TNF-related apoptosis inducing ligand (TRAIL) on their cell surface.

In the case of HPV infection, the immune response is frequently weak or undetectable, and accompanied by little or no inflammation. Even when an immune response is elicited, it may not be able to clear the virus. Disruption of the epithelial surface by frictional tissue disruption induces repair and inflammation and serves to autoinoculate the patient. Without wishing to be bound by any theory, exposure of the epithelial surface to frictional tissue disruption, uniquely induced by the apparatus and methods disclosed herein through local heating from friction forces exerted, can enhance the induction of repair, inflammation and an immune response following patient autoinoculation. Agitation or scrubbing of a lesion serves to introduce viral particles into the bloodstream of a patient, where they can trigger a humoral or antibody-related immune response. In addition, the method can fracture cells releasing antigens locally within the tissue stroma, inducing a cell mediated response associated with the release of cytokines and attraction of helper and killer T cells to the sampled tissue area.

Advantageously, the method of the present invention auto-inoculates a patient with viral particles of the specific viral serotype(s) that the patient is infected with. In contrast, current vaccine strategies are effective on a subset of HPV strains. For example, GARDASIL® by Merck & Co., Inc. is indicated to help prevent cervical cancer, precancerous and low-grade cervical lesions, vulvar and vaginal pre-cancers and genital warts caused by human papillomavirus (HPV) types 6, 11, 16 and 18, and CervarixT® by GlaxoSmithKline is an HPV 16/18 cervical cancer candidate vaccine. The vaccine is commonly injected in a limb, not the target organ at risk, the cervix, and has been only documented to elicit a humoral antibody immune reaction.

Drug Application

In some embodiments, an adjuvant drug or an immune modulating agent is used in combination with the autoinoculation method, thus augmenting an immune response. For example, Imiquimod (Aldara® topical cream, manufactured and marketed by Graceway Pharmaceutical Company) is approved for the treatment of actinic keratosis, external genital warts and superficial basal cell carcinoma (sBCC), a type of skin cancer. An immune response can be enhanced by using such immune modulating agents in combination with autoinoculation by the methods described herein. The adjuvant drug can be applied to the fenestrated loop fibers directly akin to toothpaste on a toothbrush, or a channel within the applicator can be used to transmit the drug from the top of the handle by means of a squeeze bulb or syringe, through a small lumen in the center of the fabric disc, concomitant with the tissue disruption, delivering drug into the fracture crevices created during the frictional buckling and shearing process created by the device.

Some embodiments comprise a method of drug delivery to a pathological lesion or areas of tissue that concomitantly disrupts tissue planes, creating crevices or pathways for drugs to enter via intra-epithelial and sub-epithelial spaces. This is in contrast to topical therapies, which are slowly absorbed into and through the epithelia. Intra-lesional application is more focused and requires less drug, presenting less risk of side effects.

Any type of drug (e.g., ablative, antibiotic, antiseptic, immune modulating, etc.) can be used.

In some embodiments, drug is delivered via an applicator comprising a fabric with fenestrated loops as described herein. Drug is applied in a manner akin to applying toothpaste to a toothbrush, or drug can injected onto the platform or the apparatus via a channel leading through a hollow applicator handle. The drug application apparatus can optionally have an element through which the drug is delivered (e.g., a syringe with a locking mechanism). Drug is applied to a "wound" created by frictionally agitating the tissue. In some embodiments, the fenestrated loops can be impregnated with a drug during manufacture, wherein the drug leeches out into the disrupted tissue when the fiber contacts and macerates/disrupts the tissue.

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

In another embodiment of the invention, a Radio Frequency IDentification (RFID) tag is imbedded in one or more of: the head of the FTSC device, the handle of the FTSC device, or a wrist bracelet worn by the clinician. In an embodiment of the invention, the RFID tag is used to identify the FTSC head device and thereby determine the parameters under which the FTSC device was used. In one embodiment of the invention, the RFID tag operates using an Ultra High Frequency (UHF) signal. In another embodiment of the invention, the RFID tag operates using a microwave frequency signal.

In an embodiment of the present invention, a RFID reader is present in the operating theater which can then read the RFID tags in the individual FTSC devices. In an embodiment of the invention, the RFID reader can be positioned so that the RFID tag antenna is least affected by any conducting material.

In one embodiment, the RFID tag is read-only. In another embodiment, the RFID tag contains an Electrically Erasable Programmable Read-Only Memory (EPROM), which enables both read and write functions. In an embodiment of the invention, the RFID tag is passive. In another embodiment of the invention, the RFID tag is semi-passive, containing a source of energy such as a battery to allow the tag to be constantly powered. In a further embodiment of the invention, the RFID tag is active, containing an internal power source, such as a battery, which is used to power any Integrated Circuits (ICs) in the tag and generate the outgoing signal. In another embodiment, the tag has the ability to enable location sensing through a photo sensor.

In one embodiment of the invention, means of communication with a base station is embedded in the FTSC device.

In one embodiment of the invention, the communication means utilizes one or more of a wireless local area network; a wireless wide area network; a cellular network; a satellite network; a Wi-Fi network; and a pager network. In one embodiment of the invention, a modem capable of communicating with one or more of the aforementioned networks is embedded in the FTSC device. In the following discussion the term 'cellular modem' will be used to describe the device embedded. The term 'cellular modem' will be herein used to identify any device of comparable size capable of communicating over one or more of the aforementioned networks. In one embodiment of the invention, the cellular modem can be a Code Division Multiple Access (CDMA) modem. In an embodiment of the invention, a RFID reader and associate integrated circuit processor can be embedded together with the cellular modem in the FTSC device. In such an embodiment, the RFID tags and RFID reader can be positioned to optimize the RFID read of the RFID tags from the available devices.

In an embodiment of the invention, a system for using and monitoring an FTSC device during a surgical procedure, comprises an FTSC head and handle, a comb for removing the tissue from the FTSC head, and a means for rotating the FTSC handle. The means for turning the FTSC head can include an automated device. The FTSC rotating device can include an input module for selecting parameters for use with the FTSC device, wherein the input module selects parameters based at least in part on the FTSC head device selected, a sensor for monitoring the FTSC head rotating velocity, a processor for comparing the rotational velocity of the FTSC head and the selected parameters and automatically adjusting the FTSC head rotation velocity when the comparison indicates an increased or decreased head rotation is required. The input module can receive audio, tactile or visual feedback to adjust the FTSC device during the surgical procedure.

In an embodiment of the invention, the FTSC device can be applied in any surgical, scientific, crime investigation or veterinary application that requires the use of a regulated constant or variable rotating tissue sampler. This can include laboratory equipment that requires tissue sampling, storage or any other clinical procedure.

The foregoing description of embodiments of the methods, systems, and components of the present invention has been provided for the purposes of illustration and description. It is not intended to be exhaustive or to limit the invention to the precise forms disclosed. Many modifications and variations will be apparent to one of ordinary skill in the relevant arts. For example, steps performed in the embodiments of the invention disclosed can be performed in alternate orders, certain steps can be omitted, and additional steps can be added. The embodiments were chosen and described in order to best explain the principles of the invention and its practical application, thereby enabling others skilled in the art to understand the invention for various embodiments and with various modifications that are suited to the particular used contemplated. Other embodiments are possible and are covered by the invention. Such embodiments will be apparent to persons skilled in the relevant art(s) based on the teachings contained herein. The breadth and scope of the present invention should not be limited by any of the above-described exemplary embodiments, but should be defined only in accordance with the following claims and their equivalents.

What is claimed is:

1. A device for simultaneous biopsy sampling and transepithelial drug delivery comprising:
   (a) a handle;
   (b) a head attached to the handle;
   (c) a facet associated with the head; and (d) an abrasive material comprising a plurality of fenestrated loops each including a fenestrated hook end and a fenestrated arm attached to the facet, where the plurality of fenestrated loops have a distance from the top of the plurality of fenestrated loops to the bottom of the hook end less than 20% of the length of the plurality of fenestrated loops, where the abrasive material includes a channel formed by the fenestrated arm and the fenestrated hook end to contain one or both a drug and an adjuvant.

2. The device of claim 1, where the plurality of fenestrated loops are of a length and are attached to one or both a backing material and the facet.

3. The device of claim 2, where the length is between:
a lower limit of 4 mm; and
an upper limit of 7 mm.

4. The device of claim 1, where the drug is selected from the group consisting of an ablative, an antibiotic, an antiseptic, and an immune modulating compound.

5. The device of claim 1, where the biopsy sampling and trans-epithelial drug delivery results in autoinoculation.

6. The device of claim 1, where the adjuvant is imiquimod.

7. The device of claim 1, where one or both the drug and the adjuvant are applied to the channel using an applicator.

8. The device of claim 7, where the applicator transmits one or both the drug and the adjuvant through a small lumen in the one or more regions of the abrasive material.

9. The device of claim 7, where the applicator transmits one or both the drug and the adjuvant from the handle.

10. The device of claim 9, where the applicator transmits one or both the drug and the adjuvant from the handle using a device selected from the group consisting of a squeeze bulb and a syringe.

11. A device for trans-epithelial drug delivery comprising:
(a) a handle including a proximal end and a distal end, where the handle has a principal axis of rotation, wherein the principal axis of rotation bisects the proximal end of the handle and the distal end of the handle;
(b) a head with a proximal end and a distal end, where the proximal end of the head is attached to the distal end of the handle;
(c) a facet associated with the head with a central portion, an outer portion and a perimeter; and
(d) one or more regions of an abrasive material comprising a plurality of fenestrated loops each including a fenestrated hook end and a fenestrated arm attached to the facet, where the plurality of fenestrated loops have a distance from the top of the plurality of fenestrated loops to the bottom of the hook end less than 20% of the length of the plurality of fenestrated loops, where the abrasive material includes a channel formed by the fenestrated arm and the fenestrated hook end to contain one or both a drug and an adjuvant.

12. The device of claim 11, where the plurality of fenestrated loops are of a length and are attached to one or both a backing material and the facet.

13. The device of claim 12, where the length is between:
a lower limit of 4 mm; and
an upper limit of 7 mm.

14. The device of claim 11, where the drug is selected from the group consisting of an ablative, an antibiotic, an antiseptic, and an immune modulating compound.

15. The device of claim 11, further comprising an applicator, where one or both the drug and the adjuvant are applied to the channel using the applicator.

16. The device of claim 15, where the applicator transmits one or both the drug and the adjuvant through a small lumen in the one or more regions of the abrasive material.

17. The device of claim 15, where the applicator transmits one or both the drug and the adjuvant from the handle.

18. The device of claim 17, where the applicator transmits one or both the drug and the adjuvant from the handle using a device selected from the group consisting of a squeeze bulb and a syringe.

19. A device for simultaneous biopsy sampling and trans-epithelial drug delivery comprising:
(a) a handle;
(b) a head attached to the handle;
(c) a facet associated with the head;
(d) an abrasive material comprising a plurality of fenestrated loops each including a fenestrated hook end and a fenestrated arm attached to the facet, where the plurality of fenestrated loops have a distance from the top of the plurality of fenestrated loops to the bottom of the hook end less than 20% of the length of the plurality of fenestrated loops, where the abrasive material includes a channel formed by the fenestrated arm and the fenestrated hook end; and
(e) a drug associated with the abrasive material.

20. The device of claim 19, where the drug is selected from the group consisting of an ablative, an antibiotic, an antiseptic, and an immune modulating compound.

21. The device of claim 19, where the biopsy sampling and trans-epithelial drug delivery results in autoinoculation.

* * * * *